US006777193B1

(12) United States Patent
Baeza-Ramirez et al.

(10) Patent No.: US 6,777,193 B1
(45) Date of Patent: Aug. 17, 2004

(54) METHODS FOR DIAGNOSTIC AND/OR TREATMENT OF ANTIPHOSPHOLIPIDS ANTIBODIES-RELATED DISEASES, AND DEVICES

(75) Inventors: María Isabel Baeza-Ramirez, Coloina Santo Tomas (MX); José Leopoldo Aguilar-Faisal, Colonia santo Tomas (MX); Carlos Wong Ramirez, Colonia Santo Tomas (MX); Miguel Angel Ibáñez Hernández, Colonia Santo Tomas (MX); Mónica Lara Uc, Colonia Santo Tomas (MX)

(73) Assignee: Escuela Nacional de Ciencias Biologicas, del Instituto Politecnico Nacional (MX)

( * ) Notice: Subject to any disclaimer, the term of this patent is extended or adjusted under 35 U.S.C. 154(b) by 60 days.

(21) Appl. No.: 09/632,735

(22) Filed: Aug. 4, 2000

(51) Int. Cl.[7] ........................ G01N 33/53; G01N 33/543

(52) U.S. Cl. ........................ 435/7.21; 435/7.1; 435/7.2; 435/7.94; 435/7.92; 435/174; 435/176; 435/177; 435/287.1; 435/287.2; 435/287.9; 435/975; 436/506; 436/507; 436/518; 436/519; 436/513; 436/524; 436/528; 436/533; 436/534; 436/536; 436/538; 436/547; 436/548; 436/811; 436/815; 436/829; 422/68.1

(58) Field of Search ........................ 435/7.1, 7.2, 7.21, 435/7.94, 287.9, 7.92, 174, 176, 177, 287.1, 287.2, 975; 436/519, 507, 829, 513, 506, 547, 548, 538, 536, 518, 524, 528, 533, 534, 811, 815; 422/68.1

(56) References Cited

U.S. PATENT DOCUMENTS

| | | | | |
|---|---|---|---|---|
| 4,698,299 A | * | 10/1987 | Janoff et al. ................... | 435/13 |
| 5,344,758 A | * | 9/1994 | Krillis et al. ................. | 433/4.1 |
| 5,472,883 A | * | 12/1995 | Matsuura et al. ........... | 436/518 |
| 5,506,110 A | * | 4/1996 | Matsuura et al. .......... | 435/7.94 |
| 5,561,070 A | * | 10/1996 | Stewart et al. .............. | 436/526 |
| 5,610,024 A | * | 3/1997 | Muller-Berghaus et al. .. | 435/13 |
| 5,776,487 A | * | 7/1998 | Maxfield Wilson et al. | 424/450 |
| 5,780,319 A | * | 7/1998 | Maxfield Wilson et al. | 436/519 |
| 5,840,587 A | * | 11/1998 | Stewart et al. .............. | 436/513 |
| 5,998,223 A | * | 12/1999 | Matsuura et al. ........... | 436/518 |
| 6,284,475 B1 | * | 9/2001 | Rand ......................... | 435/7.21 |

OTHER PUBLICATIONS

Aguilar et al., "Phospholipid Membranes Form Specific Nonbilayer Molecular Arrangements That Are Antigenic," The Journal of Biological Chemistry 274(36):25193–25196, 1999.
Alving, "Immunologic aspects of liposomes: presentation and processing of liposomal protein and phospholipid antigens," Biochim. Biophys. Acta 1113:307–22, 1992.
Arvieux, "Development of an ELISA for Autoantibodies to Prothrombin Showing their Prevalence in Patients with Lupus Anticoagulants," Thromb Haemost 74(4):1120–5, 1995.
Asherson et al., The Antiphospholipid Syndrome: History, Definition, Classification, and Differential Diagnosis, Chapter I, pp. 3–12, CRC Press, Inc., 1996.
Baeza et al., "Transbilayer Diffusion of Divalent Cations into Liposomes Mediated by Lipidic Particles of Phosphatidate," J. Mol. Evol. 39:560–568, 1994.
Baeza et al., "Identification of phosphatidate nonlamellar phases on liposomes by flow cytometry," Biochem. Cell Biol. 73:289–297, 1995.
Berard et al., "Plasma reactivity to hexagonal II phase phosphatidylethanolamine is more frequently associated with lupus anticoagulant than with antiphosphatidylethanolamine antibodies," J. Lab. Clin. Med. 122(5):601–605, 1993.
Bevers et al., "Lupus Anticoagulant IgG's (LA) Are Not Directed to Phospholipids only, but to a Complex of Lipid-Bound Human Prothrombin," Thromb Haemost 66(6):629–32, 1991.
Biasiolo et al., "Antiphospholipid antibodies are not present in the membrane of gel–filtered platelets of patients with IgG anticardiolipin antibodies, lupus anticoagulant and thrombosis," Blood Coagulation Fibrinolysis 4:425–428, 1993.
Cullis et al., "Lipid Polymorphism," Membrane Fusion, pp. 35–64, Marcel Dekker, New York, 1991.
Faisal, "Detección de Anticuerpos Contra Particulas Lipidicas en el Suero de Pacientes con Sindrome de Antifosfolipidos," Instituto Politecnico Nacional, Mexico, D.F., 1999.
Gibson et al., "Combined D–Penicillamine and Chloroquine Treatment of Rheumatoid Arthritis—A Comparative Study," Br J Rheumatol 26(4):279–84, 1987.
Guglielmone et al., Distribution of Lupus Anticoagulant and Anticardiolipin Antobidy Isotypes in a Population with Antiphospholipid Syndrome, The Journal of Rheumatology 26(1):86–90, 1999.
Harris et al., "Anti–phospholipid Antibodies," Clinics in Rheumatic Diseases, 11(3):591–609, Dec. 1985.
Köhler et al., "Continuous cultures of fused cells secreting antibody of predefined specificity," Nature 256:495–497, Aug. 7, 1975.

(List continued on next page.)

*Primary Examiner*—Long V. Le
*Assistant Examiner*—Kartic Padmanabhan
(74) *Attorney, Agent, or Firm*—Rothwell, Figg, Ernst & Manbeck, PC

(57) ABSTRACT

Methods for detecting anti-lipidic particles antibodies and lipidic particles in cellular membranes for the diagnosis of diseases associated to the antiphospholipid syndrome are disclosed. Kits or sets to put these methods of diagnosis into practice are also disclosed. Methods for the therapeutically treatment of diseases associated to the antiphospholipid syndrome are disclosed as well. In addition, methods for the detection of the diverse physiologic states of cells, and those kits useful for this are also disclosed.

9 Claims, 17 Drawing Sheets

OTHER PUBLICATIONS

Loizou et al., "Measurement of anti–cardiolipin antibodies by an enzyme–linked immunosorbent assay (ELISA): standardization and quantitation of results," Clin. exp. Immunol. 62:738–745, 1985.

McNeil et al., "Anticardiolipin antibodies and lupus anticoagulants comprise separate antibody subgroups with different phospholipid binding characteristics," British Journal of Haematology 73:506–513, 1989.

McNeil et al., "Anti–phospholipid antibodies are directed against a complex antigen that includes a lipid–binding inhibitor of coagulation: $\beta_2$–Glycoprotein I (apolipoprotein H)," Proc. Natl. Acad. Sci. USA 87:4120–4124, Jun. 1990.

Nakamura et al., "Lupus Anticoagulant Autoantibody Induces Apoptosis in Umbilical Vein Endothelial Cells: Involvement of Annexin V," 205(2):1488–1493, Dec. 15, 1994.

Nilsson et al, "Immunization of mice and rabbits by intrasplenic deposition of nanogram quantities of protein attached to Sepharose beads or nitrocellulose paper strips," Journal of Immunological Methods 99:67–75, 1987.

Pengo, "Autoimmune Antiphospholipid Antibodies Are Directed against a Cryptic Epitope Expressed when β2–Glycoprotein I is Bound to a Suitable Surface," Thromb Haemost 73(1):29–34, 1995.

Pierangeli et al., "Are immunoglobulins with lupus anticoagulant activity specific for phospholipids?" British Journal of Haematology 85:124–132, 1993.

Piette et al., "Exclusion Criteria for Primary Antiphospholipid Syndrome," The Journal of Rheumotology 20:1802–1804.

Pittoni et al., "Apoptosis and Antiphospholipid Antibodies," Seminars in Arthritis and Rheumatism 28(3):163–178, Dec. 1998.

Ramirez, "Caracterizacion Fisica E Inmunologica de Arreglos Moleculares de No–Bicapa en Liposomas," Instituto Politecnico Nacional, Mexico, D.F., 1994.

Ramirez et al., "Determinación de Asociaciones Lipidices de No–Bicapa en Liposomas y Membranas Celulares con Anticuerpos Monoclonales," Instituto Politecnico Nacional, Mexico, D.F., 1997.

Ramirez et al., Inducción y Caracterización de Anticuerpos Antifosfolipidos Obtenidos en Ratones BalB/c Tratados con Cloropromacina, Procainamida y Liposomas, Instituto Politecnico Nacional, Mexico, D.F., 1998.

Rauch et al., "Distinguishing Plasma Lupus Anticoagulants from Anti–Factor Antibodies Using Hexagona (II) Phase Phospholipids," Thrombosis and Haemostasis 62(3):892–896, 1989.

Rauch et al., "Inhibition of Lupus Anticoagulant Activity by Hexagonal Phase Phosphatidylethanolamine in the Presence of Prothrombin," Thromb Haemost 80:936–41, 1998.

Roubey et al., "'Anticardiolipin' Autoantibodies Recognize $\beta_2$–Glycoprotein I in the Absence of Phospholipid," Journal of Immunology pp. 954–960, 1995.

Schuber, "Influence of polyamines on membrane functions," Biochem. J. 260:1–10, 1989.

Shi et al., $\beta_2$–Glycoprotein I is a Requirement for Anticardiolipin Antibodies Binding To Activated Platelets: Differences With Lupus Anticoagulants, Blood 81(5):1255–1262, Mar. 1, 1993.

Shoenfeld et al., "Lessons from experimental APS models," Lupus 7 (Suppl. 2):S158–S161, 1998.

Sugi et al., "Autoantibodies to Phosphatidylethanolamine (PE) Recognize a Kininogen–PE Complex," Blood 86(8):3083–9, Oct. 15, 1995.

Tan et al., "The 1982 Revised Criteria for the Classification of Systemic Lupus Erythematosus," Arthritis Rhem 25(11):1271–1277, Nov. 1982.

Tincani et al., "Animal Models of the Antiphospholipid Syndrome," The Antiphospholipid Syndrome, Chapter 6, pp. 71–82, ed. by Asherson et al., CRC Press, Boca Raton, 1996.

* cited by examiner

Phosphorylcholine

Phosphorylserine

Phosphorylethanolamine

Glycerolphosphorylcholine

Glycerolphosphorylserine

METHODS FOR DIAGNOSTIC AND/OR TREATMENT OF ANTIPHOSPHOLIPIDS ANTIBODIES-RELATED DISEASES, AND DEVICES

FIELD OF THE INVENTION

The present invention relates to obtaining antibodies recognizing lipids and more particularly, is related to methods for obtaining antibodies against lipidic structures different from the lipidic bilayer, and to the use of these antibodies in diagnostic and/or treatment of diseases associated with the antiphospholipid syndrome; as well as for the determination of physiological states of the cell.

BACKGROUND OF THE INVENTION

Considering the state of the art there are different studies in which evidence of the existence of antibodies that recognize lipids can be found. For example, they have been detected in the serum of patients with antiphospholipid syndrome, as was described by Asherson et al. in their book "The antiphospholipid syndrome" in 1996 (*CRC Press*, Boca Raton). In the same way, antiphospholipid antibodies have been obtained from animals that were experimentally treated with lipids by active immunization, in accordance with Alving in 1992 (*Biochim. Biophys. Acta* 1113:307–322) or, in animals that received antiphospholipid antibodies by passive immunization, as Tincani and Shoenfeld described in 1996 in the above mentioned book.

The anti-lipid antibodies have been classified into two major subgroups according with the method used for their determination. These groups are anti-cardiolipin antibodies and anticoagulant antibodies (Guglielmone y Fernandez, 1998, *J. Rheumatol.* 26:86–90).

The anti-cardiolipin antibodies are determined by methods in which cardiolipin immobilized in a solid phase is used. This was described by Harris et al. in 1985 (*Clin. Rheum. Dis.* 11:591–609), such as the enzyme-linked immunosorbent assays and the radioimmunoassays better known by their respective initial abbreviations as ELISA and RIA which have been broadly used in the above mentioned technique.

The anticoagulant antibodies are detected by methods in which the prolongation in the coagulation time of plasma samples is measured in vitro, according with Bevers et al. 1991(*Thromb. Haemost.* 66:629–632). Some of these methods are: activated partial thromboplastin time (APTT), dilute Russell's viper venom time (dRVVT), protein C, and protein S among others. In these methods, the anticoagulant antibodies are bound to phosphatidylethanolamine or to phosphatidylserine which are intermediary factors in the blood coagulation cascade, and when the concentration of these lipids decrease due to the immune reaction, the coagulation time is prolonged.

The anti-cardiolipin antibodies have the disadvantage of producing crossed reaction with other anionic lipids such as phosphatidylserine and phosphatidylglycerol. Due to the lack of specificity for a certain type of lipid, the above mentioned antibodies are generally known as antiphospholipid antibodies.

In addition, antibodies against phosphatidylethanolamine have been detected in the sera from patients with antiphospholipid syndrome. Also, antibodies against phosphatidylcholine are detected in patients with hemolytic anemia, as was described by Sugi and McIntyre (*Blood* 86:3083–3089) and Arvieux et al. (*Thromb. Haemost.* 74:1120–1125), respectively, in 1995.

On the other hand, some studies have demonstrated that the binding of antiphospholipid antibodies to the lipidic antigen increases in the presence of a plasmatic protein. For example, in 1990, McNeil et al., determined that the binding of antibodies to the cardiolipin was markedly enhanced by the plasma protein $\beta_2$-glycoprotein I or apoprotein H (*Proc. Nat. Acad. Sci. USA* 87:4120–4124). Additionally, some anti-cardiolipin antibodies are bound directly to $\beta_2$-glycoprotein I, as was described by Roubey et al. in 1995 (*J. Immunol.* 154:954–960). These findings suggest that the anti-cardiolipin antibodies may recognize either a cryptic epitope on $\beta_2$-glycoprotein I exposed on the complex of $\beta_2$-glycoprotein I-cardiolipin, or $\beta_2$-glycoprotein I alone but with a very low affinity towards he glycoprotein, as was described by Pengo et. al. (1995, *Thromb. Haemost.* 73:29–34).

In accordance with these studies, it may be concluded that the binding of antiphospholipid antibodies to lipidic antigens is also associated with proteins. Sugi and McIntyre (op. cit., 1995) found that the proteins called kininogens are involved in the binding of antibodies to phosphatidylethanolamine, whereas the proteins that are bound to phosphatidylserine, such as prothrombin, protein C, protein S and annexin V, have been implicated in the binding of anticoagulant antibodies to phosphatidylserine, according with the studies in 1994 by Nakamura et al. (*Biochim. Biophys. Res. Commun.* 205:1488–1493) and by Roubey (*Blood* 84:2854–2867).

These studies indicate that the antigen of some antiphospholipid antibodies is really a complex formed by phospholipids and specific plasma proteins, but these proteins differ from those required for reactivity of antiphospholipid antibodies with cardiolipin. Nevertheless, in other studies, antiphospholipid antibodies that bound directly to the phospholipid have been identificated such as the anti-cardiolipin antibodies that do not require the $\beta_2$-glycoprotein I. Such studies were carried out by McNeil et al. in 1989 (*Br. J. Haematol.* 73:506–513) and by Pengo and Basiolo in 1993 (*Thromb. Res.* 72:423–430).

On the other hand, some anti-cardiolipin antibodies, purified by affinity chromatography, do not show anticoagulant activity (McNeil et al., op. cit., 1989; Shi et al., 1993, *Blood* 81:1255–1262). However, other studies demonstrated that the anti-cardiolipin and the anticoagulant antibodies were removed by adsorption with cardiolipin (Pengo and Biasiolo, op. cit., 1993; Pierangeli et al. 1993, *Br. J. Haematol.* 85:124–132).

Additionally, during studies in experimental animals, treated by passive or active immunization, the employed methods for the detection of antiphospholipid antibodies are the same as those described for the detection of human antiphospholipid antibodies. Furthermore, in these animal models, the different organs and tissues were analized by anatomical and histopathological studies, by immunofluorescent studies, and even by fetal resorption analysis and consequently the produced lessions in fetuses and placentas of the female animal models were also analyzed. These works were performed by Tincani y Shoenfeld (op. cit. 1996) and by Shoenfeld and Ziporen (*Lupus* 7:S158–S161, 1998).

The previously mentioned studies, show that the antiphospholipid antibodies described in human patients and in animal models have a broad specificity towards the lipidic antigens. This broad specificity of the antibodies may be attributed, among other causes, to the lack of specificity of the methods used for the detection of the above described antibodies.

In such methods, it has not been considered the chemical structure and the molecular association of lipidic antigens, as well as the chemical properties that the lipidic antigens have in the nature. As a consequence, in the lipidic antigens that have been used in those methods, the phospholipids are bound to artificial solid supports, such as in the ELISA and RIA methods, or they are in a molecular association that is not completely characterized, like in tests where the prolongation in the coagulation time is detected.

There are only a few studies in which the molecular structure of the phospholipid employed as antigen has been considered. For example, the reports of Rauch et al. in 1989 and in 1998 (*Thromb. Haemost.* 62:892–896 and *Thromb. Haemost.* 80:936–941, respectively) and that of Berard et al. (*J. Lab. Clin. Med.*, 1993, 122:601–605). In these reports, the authors demonstrated that the sera from some patients with systemic lupus erythematosus is inhibited in its anticoagulant activity by phosphatidylethanolamine associated in the hexagonal tubular II phase. This inhibition was not observed when the phospholipid was associated into the bilayer phase. However, the properties of the cellular membrane can not be related with the tubular association of phospholipids because this tubular lipidic association is practically incompatible with the vesicular structure of the cellular membrane, as different authors have established. In other words, in the lipidic antigens used in these studies the phospholipids are in molecular arrangements that do not correspond to the molecular arrangements that they present in the cellular membrane.

Additionally, it is well-known that the molecular structure of the plasmatic membrane of mammal cells is like an association heteropolymer formed by phospholipids, glycolipids, cholesterol, proteins and glycoproteins where the lipids are mainly in a molecular arrangement of bilayer. Nevertheless, it is also known that lipids may have molecular arrangements different to the bilayer and that such arrangements depend on the molecular geometry of the lipids and the surrounding conditions.

Cylindrical shaped lipids, such as phosphatidate, phosphatidylglycerol, phosphatidylinositol, phosphatidylcholine, phosphatidylserine, cardiolipin, sphingomyelin and diglucosyldiacylglycerides, in an aqueous media are associated in closed bilayers, or liposomes. Cylindrical lipids constitute from 60 to 70% of the membranal lipids.

On the other hand, the conic shaped lipids such as phosphatidylethanolamine, monoglucosyldiacylglycerides, and diacylglycerols, as well as the above mentioned lipids: phosphatidate, cardiolipin, phosphatidylserine, and phosphatidylglycerol but in the presence of divalent cations are assembled in the molecular phase known as hexagonal II ($H_{II}$), which corresponds to tubular cylinders packed hexagonally. While the inverted cone shaped lipids, such as lysophospholipids and gangliosides are associated in micelles. Conic and inverted conic shaped lipids represent from 30 to 40% of the membranal lipids.

Lipidic arrangements in hexagonal II or micellar phases, as well as any other structural arrangement of lipids that do not form a bilayer but that is immerse in a bilayer, are considered, for the purposes of this invention, as lipidic structures different to the lipidic bilayer or "lipidic particles", independently of the kind of lipids that are forming these structures.

In the same way, it is known that in the presence of divalent cations, drugs like chlorpromazine and procainamide, non-polar peptides, proteins such as the protein of the bacteriophage M13, cholesterol, lanthanum ions, as well as changes in temperature and in the pH, the conic lipids form molecular arrangements different to the lipidic bilayer. These lipidic arrangements are of transient nature because when the concentration of the compounds that induced their formation diminishes or when the temperature or the pH changes again, the conic shaped lipids return to the bilayer arrangement as was described by Cullis et al., in 1991 (Membrane Fusion. Marcel Dekker, New York), by Baeza et al. in 1995 (Biochem. Cell Biol. 73:289–297) and Aguilar et al., in 1999 (J. Biol. Chem. 274:25193–25196). Lipidic bilayer molecular arrangements are observed like a smooth surface by cryofracture analysis.

Lipids in general are molecules with low immunogenicity, and of the two molecular arrangements that the lipids may adopt in cellular membranes, it is considered that the lipidic bilayer will be the less immunogenic because it is the one that mainly constitutes the matrix of all cellular membranes.

However, it is known that the lipidic structures different to the bilayer, which are stabilized with divalent cations and that are observed as protuberances on the smooth surface of the bilayer by cryofracture analysis, induce the formation of antibodies that recognize the lipids that are associated in lipidic particles and they do not react with lipids associated in bilayer.

In connection with the above-mentioned studies, Baeza and their collaborators in 1995 (op. cit.) reported the elaboration of liposomes with lipid molecular arrangements different to the bilayer, as well as the antigenic activity of these molecular arrangements, because they were able to obtain polyclonal antibodies with them. By means of cytofluorometric analysis of the immune reaction they were also able to identify the presence of lipidic structures in the liposomes described, using for it anti-lipidic particles polyclonal antibodies obtained from mice sera.

To this respect, the mice were immunized by the introduction of artificially formed lipidic particles which when are present in excess caused the wanted immune reaction. Until now, it is believed that molecular arrangements different to the bilayer or lipidic particles would be also scarce immunogenics when they are present in the nature, for example in cells of human and animals, because lipidic particles are transient and therefore they would not be detected by immune systems.

Additionally, from the analysis of the above mentioned studies, one can observe that the cardiolipin is the only lipid that has been able to react with antibodies present in patients with the antiphospholipid syndrome or associated illnesses, and that the other phospholipids usually present in the cellular membrane in general require to be associated with proteins to react with the antibodies from these patients, or, they require to be associate in a molecular arrangement incompatible with the molecular structure of the cellular membrane; with the exception of the studies of Baeza and their collaborators (op. cit. 1995) on the anti-lipidic particles antibodies which react with a lipidic molecular arrangement similar to the one that has been described in cellular membranes.

To this respect, the presence in sera from patients with the antiphospholipids syndrome of anti-cardiolipin antibodies, a mitochondrial lipid, of anti-nuclear antibodies and of anti-DNA antibodies, it is indicative of the existence of previous events that cause immunologic damage to cellular membranes, with the disruption of the cells and the exhibition of the intracellular components to the immunologic system, causing the corresponding immunologic reaction that contributes to the development of the syndrome. However, up to now there have not been found studies which allow to determine the events that cause the disruption of the cellular membrane. In other words, with the existent knowledge so far it is impossible to detect the anti-cardiolipin antibodies, the anti-nuclear or even the anti-DNA antibodies before the damage that has been caused to the cell, impeding an early diagnosis and treatment of the illnesses associated with the syndrome.

Additionally, in the Doctoral Thesis presented by Leopoldo Aguilar in Dec. 17, 1997 (Determination of non-bilayer lipidic arrangements in liposomes and cellular membranes with monoclonal antibodies", Doctoral Thesis, National School of Biological Sciences, National Polytechnic Institute, México) 5 sera from patients with primary antiphospholipid syndrome and 5 sera from patients with systemic lupus erythematosus were analyzed, these illnesses were corroborated by clinical characteristics that the patients presented and by means of the detection of anti-cardiolipin antibodies, and of anti-nuclear antibodies, these last ones in the case of the sick persons with lupus. The analyzed sera from all patients also presented anti-lipidic particles antibodies, detected according to the techniques of liposomal-ELISA and of liposomal cytofluorometry described in the above mentioned Thesis.

This discovery, however, does not show any advantage for the early detection of the illnesses, since the presence of the antiphospholipid antibodies and of the anti-lipidic particles antibodies in those patients can be explained according with two hypothesis.

The first one, assumes that an unknown factor causes the destruction of the cellular membrane, which promotes the formation of lipidic particles from the membranal lipids that enter in contact with the immunologic system together with the intracellular components, with the consequent simultaneous formation of anti-lipidic particles antibodies, and anti-cardiolipin and anti-nuclear antibodies.

The second hypothesis, consists on assuming that the lipidic particles are formed in the cellular membrane before its destruction, and they would form anti-lipidic particles antibodies that would destroy the membrane, exposing the intracellular components to the immunologic system and giving place later on to the formation of anti-cardiolipin and anti-nuclear antibodies.

This second hypothesis was proposed in the Master Thesis presented by Monica Lara on Aug. 20, 1999 ("Detection of anti-lipidic particles antibodies in patients with the anti-phospholipid syndrome," Master Thesis, Escuela Nacional de Ciencias Biológicas [National School of Biological Sciences], Instituto Politécnico Nacional [National Polytechnic Institute], Mexico.

So far, none of the two hypothesis has been demonstrated, which is of supreme importance for the treatment of the illnesses, since should the second hypothesis probed to be certain, it would be possible to detect the illnesses above mentioned in their early stages, and also, it would be possible the prevention, cure or patient's improvement from such illnesses.

Derived from the above-mentioned hypothesis, it has been aimed to suppress the inconveniences of the induction and detection of antiphospholipid antibodies techniques caused by the structure and molecular association of the antigens used in these methods, by the employment of lipidic antigens with a structure and molecular association similar to the one found in patients with illnesses associated with antiphospholipids antibodies. These novel lipidic antigens have been used for the induction and detection of anti-lipidic particles antibodies that allow an early diagnosis of these illnesses, as well as for the determination of physiologic states of the cell, as apoptosis, or programmed cellular death (Pittoni and Isenberg, 1998, Semin. Arthritis. Rheum. 28:163–178) and those which are present in the cellular cycle (Go, G1, G2 and M) among others.

OBJECTS OF THE INVENTION

Keeping in mind the deficiencies in the structure and in the molecular association of the antigens that are used in the techniques of induction and detection of antiphospholipid antibodies from the methods of the previous techniques, one of the objectives of the present invention consists on using lipidic antigens with a structure and molecular association similar to the one that is present in patients with illnesses associated with antiphospholipid antibodies, with the purpose of providing a method for the detection of anti-lipidic particles antibodies.

It is another objective of the present invention, to provide a diagnosis method which uses monoclonal antibodies specific to lipidic antigens that respond in the same way that the anti-lipidic particles antibodies present in sera from patients with diverse illnesses associated with antiphospholipid antibodies, with the purpose of designing a strategy for the treatment of these patients against such illnesses.

It is an additional objective of the present invention, to provide a kit or diagnosis set for the detection of anti-lipidic particles antibodies in early stages of illnesses that present such antibodies in animals and in humans.

It is another objective of the present invention, to provide a kit or diagnosis set for th detection of lipidic particles in the membranes of the cells of ill entities, human or animal, that present anti-lipidic particles antibodies.

It is still another objective of the present invention, to provide a method for the prevention, cure or patient's improvement from such illnesses by means of the inhibition or the blockage of anti-lipidic particles antibodies.

Another objective of the present invention still consists on providing a method for the prevention, cure or patient's improvement from such illnesses, by means of the stabilization of cellular membranes that impedes the formation of lipidic particles and therefore the later formation of anti-lipidic particles antibodies.

An additional objective of the present invention consists on providing methods and its corresponding kits for the detection of the different physiologic states that can present the cells, which can lead to the prevention of illnesses related with antiphospholipid antibodies.

DETAILED DESCRIPTION OF THE PREFERRED EMBODIMENTS

Figure 1:
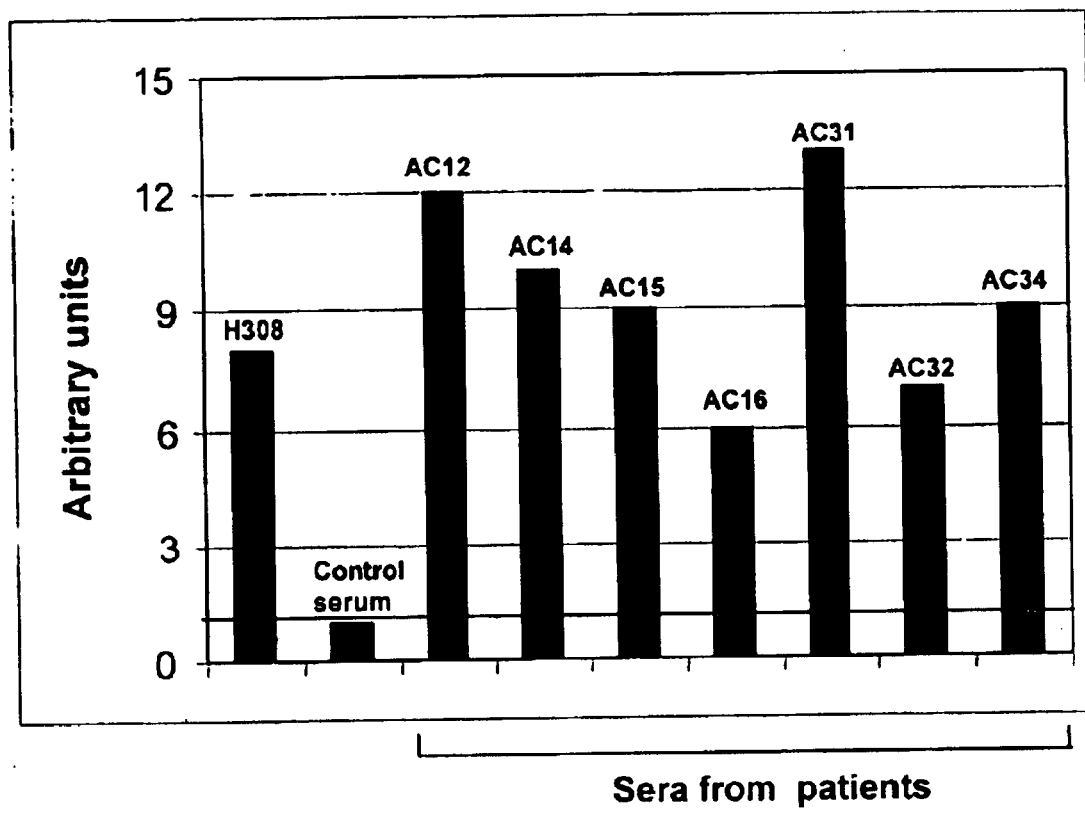
FIG. 1 shows the analysis by the liposomal-ELISA method of the reaction between control sera from human healthy blood donors, or sera from patients with the antiphospholipid syndrome, and liposomal antigens made from egg-yolk phosphatidyl-choline:phosphatidate [PC:PA] (2:1 mole ratio) bearing lipidic particles induced by calcium. Furthermore, the reaction of H308 monoclonal antibody with these antigens is also indicated.

Despite the transitory nature of lipidic particles in active cellular membranes, it has been found surprisingly that sera from patients that present illnesses associated with the antiphospholipid syndrome react with C5337 human pancreas cancer cells, which is indicative of a prolonged presence of lipidic particles in cellular membranes of these patients.

Equally, when an antigen that contains lipidic particles is administered in BALB/c mice it has been found surprisingly that these mice developed alopecia and lesions on the face in the form of butterfly wings, similar to those described in some human autoimmune illnesses, as well as deposits of immune complexes and pathological alterations in their different organs. Additionally, it has been also found that these mice firstly developed anti-lipidic particles antibodies and subsequently anti-cardiolipin antibodies, lupus anticoagulant and anti-nuclear antibodies, which confirms that anti-lipidic particles antibodies constitute the first stage in the development of illnesses associated with antiphospholipid antibodies.

According to the above-mentioned experiments, the presence of anti-lipidic particles antibodies in one of the first stages of the illness, indicates that one of the first events that occurs in the antiphospholipid syndrome is the formation of anti-lipidic particles antibodies. These antibodies when reacting with lipidic particles in cellular membranes, cause damage in these membranes, and finally cells disruption and the exhibition of the intracellular components to the immunitary system; which explains the subsequent presence of anti-cardiolipin antibodies, where cardiolipin is a mitochondrial lipid, of anti-nuclear and anti-DNA antibodies, which have been reported as present in these illnesses in humans.

For the purposes of the present invention, we understand as "illness associated with antiphospholipid antibodies" to any illness that presents antiphospholipid antibodies in any development step. Some of such illnesses are mentioned next, in an enunciative fashion, but not limitative: primary or secondary antiphospholipid syndrome; in the last case, associated with autoimmune illnesses such as vasculitis, rheumatoide arthritis and systemic lupus erythematosus; illnesses that cause an increase in the cellular division, as they can be neoplasias of the type of carcinoma in liver or in ovary, lymphomas, leukemias or myeloproliferative disorders; viral infections as mononucleosis infectious and the acquired immunodeficiency syndrome; illnesses taken place by bacteria, as syphilis; and, illnesses taken place by protozoa as malaria. Additionally, the presence of antiphospholipid antibodies has been related with myocardial infarction and senility.

Therefore, an aspect of the present invention is to develop a diagnosis method for determining if an individual having clinical characteristics of the primary antiphospholipid syndrome (Table 1), or one of the illnesses associated to the secondary antiphospholipid syndrome (Table 1) and who does not present yet anti-cardiolipin antibodies, lupus anticoagulant, anti-DNA or anti-nuclear antibodies, does have an illness associated to the presence of antiphospholipid antibodies; where such method comprises the steps of detecting in a direct or indirect fashion the presence or absence of lipidic particles in a sample from said individual, and to observe whether lipidic particles are detected or not, where the presence of said lipidic particles indicates the development of an illness associated to the presence of antiphospholipid antibodies in said individual.

In a preferred embodiment, the detection of lipidic particles is carried out in an indirect fashion by means of the use of an antigen containing lipidic particles reacting with the serum of the subject with the purpose of determining if in this serum anti-lipidic particles antibodies exist, such a determination being carried out preferably by means of the use of at least one technique selected from the group consisting of ELISA, cytofluorometry, and immunofluorescence.

In a specific embodiment, the antigen containing lipidic particles is selected among neoplastic cells and liposomes where liposomes are formed starting from at least one lipid susceptible to change its molecular geometry by means of changes in temperature, presence of divalent cations, and/or drugs. This lipid being selected preferably among phosphatidate; cardiolipin; phosphatidylglycerol; phosphatidylinositol; diacylglycerol; sphingomyelin; phosphatidylserine; monoglucosyldiacylglyceride or phosphatidylethanolamine. In a favorite modality, this lipid is found in abundance in cellular membranes.

In a specific embodiment, lipids used to form liposomes are selected according to their availability in cellular membranes and against which anti-lipid antibodies have been detected in humans, using preferably one lipid with a cylindrical molecular shape in combination with one lipid with a conical molecular shape in a mole ratio between 1:1 to 4:1. In an additional modality, a combination of phosphatidylcholine with phosphatidate from egg yolk in a 2:1molar ratio is used.

In another additional embodiment, at least an anti-lipidic particles polyclonal or monoclonal antibody is made to react with neoplastic cells or liposomal antigens to confirm the presence or not of anti-lipidic particles antibodies in the individual serum.

In another preferred embodiment, the detection of lipidic particles is carried out in a direct fashion making react cells from the subject with at least an anti-lipidic particles polyclonal or monoclonal antibody, preferably by means of the use of at least one technique selected from the group consisting of immunofluorescence, cytofluorometry and ELISA.

In an additional embodiment, besides cells of the subjects, it is made to react with the anti-lipidic particles antibodies at least an antigen that contains lipidic particles, preferably selected between neoplastic cells and liposomes with at least one lipid susceptible to change its molecular geometry by means of changes in temperature, presence of divalent cations, and/or drugs, this lipid being selected preferably among phosphatidate; cardiolipin; phosphatidylglycerol; phosphatidylinositol; diacylglycerol; sphingomyelin; phosphatidyl-serine; monoglucosyldiacylglyceride or phosphatidylethanolamine In a specific embodiment, lipids used to form liposomes are selected according to their availability in cellular membranes and against which anti-lipid antibodies have been detected in humans, using preferably a cylindrical lipid in combination with a conical lipid in a mole ratio between 1:1 to 4:1. In an additional modality, a combination of phosphatidylcholine with phosphatidate from egg yolk in a 2:1molar ratio is used.

To obtain liposomes that are used in several modalities of the present invention, it is used preferably the reverse phase evaporation method, modified by Baeza and collaborators in 1994 (*J. Mol. Evol.*, 39:560–568), and subsequently liposomes are treated with a lipidic particles inducer agent, preferably selected between divalent cations and drugs, preferably those that produce the lupus induced by drugs in humans, or combinations of the same ones; where the procedure to form lipidic particles is carried out preferably by means of incubation of liposomes with an effective quantity of the lipidic particles inducer agent at a temperature between 25 to 40° C., this effective quantity being preferably in a mole ratio lipids: lipidic particles inducer agent from 1:0.01 up to 1:300.

On the other hand, anti-lipidic particles polyclonal antibodies useful for diverse modalities of the present invention, are obtained by any known mice immunization method, using an antigen that contains lipidic particles, preferably by means of a immunization procedure of the type described by Baeza and collaborators (op. cit., 1995), which comprises:

A) A first step of mice immunization using intrasplenic injection of an effective dose of liposomes obtained from lipids against which anti-lipid antibodies have been detected in humans, where these liposomes contains lipidic particles in their surface.

B) A second step of mice immunization using intraperitoneal injection of the same liposomes and with the same doses used by the first immunization step.

When concluding these steps, immunized mice present anti-lipidic particles polyclonal antibodies which can be detected by liposomal-ELISA method and/or liposomal cytofluorometry method.

In a specific embodiment, the effective liposomes doses were from 50 to 200 mg, preferably incubated in a solution from 0.1 to 10 mM of $CaCl_2$, $MnCl_2$, chlorpromazine, procainamide or combinations of the same ones in the presence of a buffer solution with pH between 7.0 to 7.4.

In an additional embodiment, in the first immunization step it is necessary to administer liposomes at least 2-times by intrasplenic injection with intervals of 1-week, and in the second immunization step it is necessary to introduce liposomes by intraperitoneal injection at least 4-times with intervals of 2-weeks, according to the method described by Nilsson et al. in 1987 (*J. Immunol. Methods* 99:67–75) and modified by Aguilar in 1994 (Physical and immunologic characterization of non-bilayer molecular arrangements in liposomes", Master Thesis, National School of Biological Sciences, National Polytechnic Institute, México).

In another additional embodiment, mice used for immunization, were selected from singenic strain, using preferably 2-months age BALB/c female mice.

Starting from the immunized mice, it is possible to obtain monoclonal antibodies by means of any well-known method, preferably by means of the obtention of a hybridoma. In a specific modality, the hybridoma was obtained according with the following steps:

A) Mice that were immunized by intrasplenic and intraperitoneal injections received a third immunization by intravenous administration of the liposomes doses used for the first and second immunization steps.

B) A fusion step of immunized mouse spleen cells with myeloma mouse cells that do not secrete gamma chains neither kappa chains. This fusion was carried out at least 4-days after the intravenous immunization to obtain at least a hybridoma producing an anti-lipidic particles monoclonal antibody.

C) A step of hybridomas selection, in which the hybridoma is selected among those which present detectable immunoreaction, using for the detection of anti-lipidic particles antibodies the liposomal-ELISA method and/or the cytofluorometry method.

In a specific embodiment, the effective liposomes doses were between 50 to 200 mg, and preferably incubated with a solution from 0.1 to 10 mM of $CaCl_2$, $MnCl_2$, chlorpromazine, procainamide or combinations of the same ones in presence of a buffer solution with pH between 7.0 to 7.4.

In an additional embodiment, the first immunization step include the administration of liposomes at least 2-times by intrasplenic injection with intervals of 1-week, and the second immunization step include the introduction of liposomes by intraperitoneal injection at least 4-times with intervals of 2-weeks, using the method described by Nilsson et al. (op. cit., 1987) and modified by Aguilar (op. cit., 1994).

In another additional embodiment, mice used for immunization, were selected from singenic strain, using preferably 2-months age BALB/c female mice.

In a preferred embodiment of the present invention, immunized mouse spleen cells were obtained according to the procedure described by Aguilar (op. cit., 1997), by dispersion of the mouse spleen in an appropriate cellular culture medium, preferably incomplete DMEM medium or RPMI medium added with glutamine 200 mM and glycine 100 mM, followed by diverse purification steps and of an erythrocytes lysis, preferably with ammonium chloride, which only disrupted erythrocytes without affecting lymphocytes neither leukocytes in general.

Cells of the P3X63Ag8U.1 cellular line of mouse myeloma obtained by Yeltan (*Curr. Top. Microbiol. Immunol.*, 1978, 81:1–7) are preferably used. This cellular line is derived from the cellular line obtained by Kohler and Milstein (*582 Nature*, 1975, 256:495–497) from BALB/c female mice MOPC21 myeloma.

Regarding the method used for cellular fusion, preferably the one described by Aguilar (op. cit., 1997) is used, this method consists in using the immunized mouse spleen and myeloma cells with a viability higher than 95%, which are centrifuged and mixed in a cellular proportion 1:1, to be subsequently subjected to diverse washes steps and cultivated in cellular culture microtiter plates previously seeded with macrophages.

With respect to the methods used for the detection of anti-lipidic particles antibodies in patients sera by means of the use of antigens that contain lipidic particles, or for the detection of lipidic particles in cells from patients by using anti-lipidic particles antibodies, the favorite techniques will be next described for such detections.

It is important to point out that in the description of these techniques the term "antibody porter" refers to any fluid susceptible of containing anti-lipidic particles antibodies, as it can be a plasm or a serum from human or from animal origin, a solution or a suspension; while the term "antigen" refers to those structures susceptible of containing lipidic particles such as liposomes or cells.

Additionally, it is also important to point out that in a specific modality of the present invention, before start using any detection method, an inactivation of sera or of plasms was carried out by increasing their temperature, preferably subjecting sera or plams at temperatures between 50 to 60° C. for 0.25 to 1 h.

On the other hand, the liposomal-ELISA method (Aguilar, op. cit., 1994; 1997; Aguilar et al., op. cit., 1999), as its name indicates, it is applicable in those cases in which the antigen is a liposome, independently of the origin of the antibody porter, and it comprises the following steps:

A) A first step of addition and incubation, in which an effective quantity of an antigen suspension is added to each one of the wells of the ELISA microtiter plate. This microtiter plate selected among those with a high lipidic antigens binding property and said microtiter plate is incubated between 25 to 30° C. for 0.25 to 2 h.

B) A second step of addition and incubation, in which an effective quantity of a blocking solution is added to each one of the wells of the ELISA microtiter plate with a high lipidic antigens binding property, and said microtiter plate being incubated at a temperature between 25 to 30° C. for 0.25 to 2 h.

C) A step of elimination of blocking solution, preferably by suction, with caution to avoid that microtiter plate becomes dry when blocking solution is eliminated, because liposomal antigens can be damaged.

D) A third step of addition and incubation, in which an effective quantity of the antibody porter is quickly added, to avoid that microtiter plate becomes dry, to each one of the wells using an antibody porter dilution from 1:5 to 1:1000 into blocking solution; said microtiter plate being incubated for 0.25 to 2 h at a temperature between 25 to 30° C.

E) A first step of washing, in which the microtiter plate is washed with the blocking solution, preferably repeating 4-times and avoiding that microtiter plate becomes dry when eliminating the blocking solution.

F) A fourth step of addition and incubation, in which an effective quantity of a second antibody is added to each one of the wells of microtiter plate. This plate is incubated in the darkness for 0.25 to 2 h at a temperature between 25 to 30° C. Second antibody is selected preferably among antibodies from a different specie to that of the antibody porter and they can be anti-Fc of human IgG, IgA and IgM or of the animal in study, or antibodies anti-Fc of IgM or of IgG depending on the nature of the monoclonal antibody when this is the antibody porter. Second antibody is used at a final dilution into blocking solution between 1:000 and 1:3500 and it is conjugated to an enzyme preferably to peroxidase.

G) A second step of washing, in which the microtiter plate is washed with blocking solution, preferably repeating 4-times and avoiding that microtiter plate becomes dry when eliminating the blocking solution.

H) A fifth step of addition and incubation, in which an effective quantity of the peroxidase substrates is added to each one of the wells and said microtiter plate is incubated for 0.1 to 0.5 h at a temperature between 35 and 40° C., stopping the peroxidase reaction by adding an effective quantity of sulfuric acid.

I) A step of analysis, in which microtiter plate is analyzed in a reading device for ELISA, preferably at 492 nm.

In a specific embodiment, the antigen suspension is obtained by suspending liposomes in a buffer solution at pH between 7.0 to 7.4, in a relationship from 1 to 5 mmole of the antigen per liter of buffer solution.

The blocking solution, includes a buffer solution at pH between 7.0 to 7.4, and at least a solution with a high content of proteins, preferably gelatin at 0.4%, weight by volume, with or without an effective quantity of a lipidic particles inducer agent, preferably with the effective quantity and the lipidic particles inducer agent used to form the antigen.

In a preferred embodiment, the effective quantity of the antigen suspension in the stage A it is of 50 to 100 $\mu$l. The second antibody can be also conjugated to the enzyme alkaline phosphatase, instead of peroxidase, in this case the corresponding alkaline phosphatase sustrates are used.

Liposomal-ELISA method allows the simultaneous determination of anti-lipidic particles antibodies in at least 40 sera samples, each one by duplicate, in a single microtiter plate, therefore, this method can be easily applied to the diagnosis of illnesses where this type of antibodies are present.

On the other hand, the liposomal cytofluorometry method (Baeza and collaborators., op. cit., 1995), as its name indicates, it is applicable in those cases in which the antigen is a liposome, independently of the origin of the antibody porter, and it includes the following steps:

A) A first step of addition and incubation, in which the antibody porter is added to the antigen suspension. This antibody porter is diluted from 1:5 to 1:1000 into a buffer solution at pH between 7.0 to 7.4, and the resulting mixture is incubated for 0.25 to 2 h at a temperature between 35 and 40° C.

B) A first step of washing, in which the antigen bound to the antibody porter is washed with a buffer solution at pH between 7.0 to 7.4, with or without an effective quantity of a lipidic particles inducer agent, preferably with the same quantity and the same inducer agent used to obtain the antigen.

C) A step of recovery, in which the antigen bound to the antibody porter is recovered preferably by centrifugation.

D) A second step of addition and incubation, in which an effective quantity of a second antibody is added to the antigen bound to the antibody porter. The resulting mixture is incubated for 0.25 to 2 h in the darkness at a temperature between 35 to 40° C. Second antibody is selected preferably among antibodies from a different specie to that of the antibody porter and they can be anti-Fc of human IgG, IgA and IgM or of the animal in study, or antibodies anti-Fc of IgM or of IgG depending on the nature of the monoclonal antibody when this is the antibody porter. Second antibody is used at a final dilution from 1:25 to 1:500 into a buffer solution at pH between 7.0 to 7.4, and it is conjugated to a substance or fluorescent substratum, preferably to fluorescein isothiocyanate (FITC).

E) A second step of washing, in which the antigen bound to the antibody porter and to the second antibody is washed with a buffer solution at pH between 7.0 to 7.4, with or without an effective quantity of a lipidic particles inducer agent, preferably with the same quantity and the same inducer agent used to obtain the antigen.

F) A step of suspension and analysis, in which the antigen bound to the antibody porter and the second antibody is suspended in a transporting solution, selected preferably between FACS Flow (Beckton Dickinson Co.) and Haema Line 2 (Serotono-Baker Diagnostics, INC) in a relationship from 1 to 5 mmole of the antigen in a liter of solution; this solution being preferably filtered previously with a 0.22 $\mu$m Millipore filter pore diameter, the obtained mixture being analyzed in a flow cytometer, preferably with a single 488 nm argon laser beam.

In a preferred embodiment, the antigen suspension is obtained suspending liposomes in a buffer solution at pH between 7.0 to 7.4, in a relationship of 1 to 5 mmole per liter of buffer solution. Furthermore, the fluorescent sustrate can also be selected from the group consisting of phycoerythrin, Cy3 and Percp.

Liposomal cytofluorometry method has a sensibility 10-fold higher than liposomal-ELISA method in the detection of anti-lipidic particles antibodies. Therefore, this method must be applied when some doubtful result has been obtained with the liposomal-ELISA method. Cytofluorometry method also allows to analyze the presence of lipidic particles in liposomal or cellular antigens, as well as to compare the different types of reaction of polyclonal or monoclonal antibodies with the lipidic particles of these antigens.

In another preferred embodiment of cytofluorometry method, the suspension of the antigen can be from human or animal cells, and the suspension of the antigen is obtained by suspending the cells, preferably isolated cells as erythrocytes, leukocytes and even plaquettes in a buffer solution at pH between 7.0 to 7.4. With the exception of this difference regarding the antigen, the steps of this cytofluorometry method are as those described in subparagraph (A) to (F) for liposomal cytofluorometry method in which liposomes are used as antigens.

Regarding cellular methods, the immunofluorescence method for cells, applicable when the antigen is a cell, comprises the following steps:

A) A step of cells culture, in which an effective quantity of the antigen is placed, preferably 1×10$^6$ cells, in a micro covers glass inside each well of a cell culture plate and it is incubated under an atmosphere containing an effective $CO_2$ quantity at a temperature between 35 to 40° C. until cellular confluence reaches 90%.

B) A first step of washing, in which the antigen is washed with an appropriate cell culture medium, preferably repeating 2-times, and with a phosphates buffer solution at pH between 7.0 to 7.4, under sterility conditions. Avoiding that the surface of cellular culture becomes dry when eliminating the phosphates buffer solution, which can damage cellular antigens.

C) A first step of addition and incubation, in which an effective quantity of an antibodies porter is added to the cellular antigen, preferably 50 to 200 $\mu$l without dilution or with a maximum dilution of 1:1000 into an appropriate cell culture medium. Cellular antigens treated with the antibody porter are incubated under an atmosphere containing an effective $CO_2$ quantity for 0.25 to 2 h at a temperature between 35 to 40° C.

D) A second step of washing, in which the antigen bound to the antibody porter is washed with a phosphates buffer solution at pH between 7.0 to 7.4. Preferably repeating 3-times and avoiding that the surface of the cellular culture becomes dry when eliminating the phosphates buffer solution.

E) A second step of addition and incubation, in which an effective quantity of a second antibody is added to the antigen bind to the antibody porter. The mixture obtained is incubated under an atmosphere containing an effective $CO_2$ quantity for 0.25 to 2 h at a temperature between 35 to 40° C. The second antibody is selected preferably among antibodies from a different specie to that of the antibody porter and they can be anti-Fc of human IgG, IgA and IgM or of the animal in study, or antibodies anti-Fc of IgM or of IgG depending on the nature of the monoclonal antibody when this is the antibody porter. Second antibody is used at a final dilution from 1:25 to 1:500 into an appropriate cell culture medium and it is conjugated to a substance or fluorescent substratum, preferably to FITC.

F) A third step of washing, in which the antigen bound to the antibody porter and to the second antibody is washed with a phosphates buffer solution at pH between 7.0 to 7.4. Preferably repeating 3-times and avoiding that the surface of the cellular culture becomes dry when eliminating the phosphates buffer solution.

G) An step of analysis, in which micro covers glass is mounted preferably on a slide with a fluorescence protector such as VectaShield to be observed in a confocal microscope, or with epifluorescence and optics of Nomarski.

In a specific embodiment, the effective quantity of $CO_2$ is attained with 1 to 10% in volume with regard to air, while the effective quantity of phosphates buffer solution is attained with 1 to 10 ml. The fluorescent substrate can also be selected from the group consisting of phycoerythrin, Cy3 and Percp.

In another preferred embodiment of the immunofluorescence method, microsections of an organ from humans or animals can be used as antigen, instead of a cellular culture as it was described previously. With the exception of this difference regarding the antigen, the steps of this immunofluorescence method are as those described in subparagraphs (B) to (G) for the immunofluorescence method in which a cellular culture is used as antigen.

Finally, the cellular-ELISA method includes the following steps:

A) A step of culture, in which an effective quantity of cellular antigen is added to each one of the wells of a microtiter plate, preferably $1 \times 10^5$ cells, this antigen being cultivated until the confluence in the wells reaches 100%.

B) A first step of addition and incubation, in which an effective quantity of a blocking solution is added to each one of the wells of microtiter plate, and said plate is incubated between 35 to 40° C. for 0.5 to 1 h.

C) A step of elimination of blocking solution, avoiding that the surface of the cellular culture becomes dry when eliminating the blocking solution, which can damage cellular antigens.

D) A second step of addition and incubation, in which an effective quantity of an antibody porter is added to each one of the wells of microtiter plate in an antibody porter dilution from 1:5 to 1:1000 into blocking solution; said microtiter plate being incubated for 0.25 to 2.0 h at a temperature between 35 to 40° C. in presence of an effective quantity of $CO_2$.

E) A first step of washing, in which cell cultures are washed with the blocking solution, preferably repeating 3-times and avoiding that the surface of the cellular culture becomes dry when eliminating the blocking solution.

F) A third step of addition and incubation, in which an effective quantity of a second antibody is added to each one of the wells of microtiter plate. This plate is incubated for 0.25 to 2 h at a temperature between 35 to 40° C. in presence of an effective quantity of $CO_2$. Second antibody is selected preferably among antibodies from a different specie to that of the antibody porter and they can be anti-Fc of human IgG, IgA and IgM or of the animal in study, or antibodies anti-Fc of IgM or of IgG depending on the nature of the monoclonal antibody when this is the antibody porter. Second antibody is used at a final dilution from 1:1000 to 1:3500 into blocking solution and is conjugated to an enzyme preferably peroxidase.

G) A second step of washing, in which microtiter plate is washed with the blocking solution, preferably repeating 3-times and avoiding that the surface of the cellular culture becomes dry when eliminating the blocking solution.

H) A fourth step of addition and incubation, in which an effective quantity of peroxidase substrates is added to each one of the wells of microtiter plate, being incubated said plate for 0.1 to 0.5 h at a temperature between 35 to 40° C., stopping the peroxidase reaction by means of an effective quantity of sulfuric acid.

I) A step of analysis, in which microtiter plate is analyzed in a reading device for ELISA, preferably at 492 nm.

In a specific embodiment, the effective quantity of $CO_2$ is attained with 1 to 10% in volume wit regard to air, while the effective quantity of phosphates buffer solution is attained with 1 to 10 ml.

The blocking solution, includes a buffer solution at pH between 7.0 to 7.4, and at least a solution with a high content of proteins, preferably fetal calf serum at 5%, volume by volume, with or without an effective quantity of a lipidic particles inducer agent, selected preferably among solutions from 0.1 to 10 mM of $CaCl_2$, $MnCl_2$, chlorpromazine, procainamide or combinations of the same ones.

On the other hand in another specific modality of this method, the second antibody can be conjugated to the enzyme alkaline phosphatase, instead of peroxidase, in this case the corresponding alkaline phosphatase substrates are used.

Another aspect of the present invention, is to develop an in vitro diagnosis instrument for illnesses associated with antiphospholipid antibodies, useful to carry out the method of the present invention. This diagnosis instrument includes at least an indicator reagent to detect the presence of lipidic particles or anti-lipidic particles antibodies in a sample of an individual having clinical characteristics of primary antiphospholipid syndrome (Table 1), or of the illnesses associated to secondary antiphospholipid syndrome (Table 1) and who does not present yet anti-cardiolipin antibodies, lupus anticoagulant, anti-DNA or anti-nuclear antibodies; media to allow the reaction of the sample with the indicator reagent; and, procedures to make evident this reaction.

In a preferred embodiment, the indicative reagent is selected among liposomes with lipidic particles in their surface, neoplastic cells, anti-lipidic particles polyclonal antibodies, and/or anti-lipidic particles monoclonal antibodies.

In another preferred embodiment, the sample is selected among cells and plasma or serum of the individual. Furthermore, the medium to allow the reaction include at least a regulating solution of the reaction and at least a device to keep the reagent, the sample and the regulating solution.

The regulating solution is selected preferably among buffer solutions at pH between 7.0 to 7.4, with or without a lipidic particles inducer agent, and phosphate buffer solutions at pH between 7.0 to 7.4, with or without a lipidic particles inducer agent.

On the other hand, the device to keep the reagent, the sample and the regulating solution is selected preferably among tubes for centrifugation, microtiter plates containing micro cover glasses; ELISA microtiter plates with a high lipidic antigens binding property; and, microtiter plates for cellular-ELISA. In the modality in which ELISA microtiter plates and/or cellular-ELISA microtiter plates are used, the diagnosis set also includes a blocking solution that includes a buffer solution at pH between 7.0 to 7.4, a solution with a high content of proteins, and an effective quantity of a lipidic particles inducer agent, the proteins preferably being selected between gelatin and fetal calf serum at a concentration of 0.4 to 5%, weigh by volume, or volume by volume, respectively.

On the other hand, the procedures to make evident the reaction are selected between fluorescent procedures and enzymatic procedures, preferably reactions of antibodies conjugated to a fluorochrome, preferably to fluorescein isothiocyanate or conjugated to an enzyme, preferably to peroxidase.

Regarding the individual sample, this is selected preferably between plasma or serum of the ill subject and cells from organs of the ill individual.

An additional aspect of the present invention, consists of preventing or treating illnesses associated with antiphospholipid antibodies by means of the administration of a therapeutically effective quantity of a drug for inhibition or blocking of the anti-lipidic particles antibodies from sick persons, or, by means of the administration of a therapeutically effective quantity of a stabilizer drug to achieve the stabilization of cellular membranes from sick persons. The above-mentioned processes are achieved in vitro by means of inhibition or blocking of the anti-lipidic particles antibodies from sick persons with phosphorylated haptens, which are chemical substances that are part of the polar region of the cellular membrane lipids; in a similar way as it has been demonstrated in the inhibition of H308 monoclonal antibody by phosphorylcholine and glycerolphosphoryl-choline haptens (Aguilar, op. cit. 1997).

Regarding the stabilization of cellular membranes, a therapeutically effective quantity of antimalaric drugs, which have also been used in the treatment of some illnesses of the antiphospholipid syndrome, as rheumatoid arthritis and systemic lupus erythematosus (Gibson et al., 1987, *Br. J. Rheumatol.* 26:279–285), is used. Among these drugs, it is possible to mention: chloroquine, hydroxichloroquine, amodiaquin, quinacrine or primaquine; or polyamines such as putrescine, spermidine or spermine; these polyamines are polycations which stabilize cellular membranes (Schuber, 1989, *Biochem. J.* 260:1–10). Both type of drugs avoid the formation of lipidic particles in membranal models such as liposomes or in cellular membranes, which avoids the subsequent binding of anti-lipidic particles antibodies, according with studies carry out by our investigation group.

When "a therapeutically effective quantity" of a drug with inhibitory properties is used in the present invention, it means a quantity of the inhibitor drug that when is administered to a ill subject produces the blocking of anti-lipidic particles antibodies circulating in the blood stream of the subject under treatment. "A therapeutically effective quantity" of a stabilizer drug, is a quantity of the stabilizer drug that when it is administered to an ill subject it produces the stabilization of cellular membranes in the individual under treatment, so that more anti-lipidic particles antibodies are no longer generated in this subject; or that the anti-lipidic particles antibodies present in the ill individual no longer react with cellular membranes because these membranes no longer present lipidic particles.

Studies on inhibition of anti-lipidic particles antibodies were carried out using liposomes as antigens and the antigen-antibody reaction was analyzed by the liposomal-ELISA method, which includes the following steps:

A) A first step of addition and incubation, in which an effective quantity of an antigen suspension is added to each one of the wells of the ELISA microtiter plate. This microtiter plate is selected among those with a high lipidic antigens binding property and said microtiter plate is incubated between 25 to 30° C. for 0.25 to 2 h.

B) A second step of addition and incubation, in which an effective quantity of a blocking solution is added to each one of the wells of the ELISA microtiter plate with a high lipidic antigens binding property, and said microtiter plate being incubated at a temperature between 25 to 30° C. for 0.25 to 2 h.

C) A step of elimination of blocking solution, preferably by suction, avoiding that microtiter plate becomes dry when blocking solution is eliminated, because liposomal antigens can be damaged.

D) A step of inhibition of the antibody porter, in which the antibody porter is incubated with a chemical substance, or hapten, that will inhibit the active site that recognizes the antigen in the antibody porter.

E) A third step of addition and incubation, in which an effective quantity of the antibody porter inhibited by the hapten was quickly added, to avoid that microtiter plate becomes dry, to each one of the wells using an antibody porter dilution from 1:5 to 1:1000 into blocking solution. This microtiter plate being incubated for 0.25 to 2 h at a temperature between 25 to 30° C.

F) A first step of washing, in which the microtiter plate is washed with the blocking solution, preferably repeating 4-times and avoiding that microtiter plate becomes dry when eliminating the blocking solution.

G) A fourth step of addition and incubation, in which an effective quantity of a second antibody is added to each one of the wells of microtiter plate. This plate is incubated in the darkness for 0.25 to 2 h at a temperature between 25 to 30° C. Second antibody is selected preferably among antibodies from a different specie to that of the antibody porter and they can be anti-Fc of human IgG, IgA and IgM or of the animal in study, or antibodies anti-Fc of IgM or of IgG depending on the nature of the monoclonal antibody when this is the antibody porter. Second antibody is used in a final dilution into blocking solution between 1:000 and 1:3500 and it is conjugated to an enzyme preferably to peroxidase.

H) A second step of washing, in which the microtiter plate is washed with the blocking solution, preferably repeating 4-times and avoiding that microtiter plate becomes dry when eliminating the blocking solution.

I) A fifth step of addition and incubation, in which an effective quantity of the peroxidase sustrates is added to each one of the wells and this microtiter plate is incubated for 0.1 to 0.5 h at a temperature between .35 and 40° C., stopping the peroxidase reaction by adding an effective quantity of sulfuric acid.

J) A step of analysis, in which microtiter plate is analyzed using a reading device for ELISA plates, preferably at 492 nm.

In a specific embodiment, the antigen suspension is obtained by suspending liposomes in a buffer solution at pH between 7.0 to 7.4, in a relationship from 1 to 5 mmole of antigen per liter of buffer solution.

The blocking solution, includes a buffer solution at pH between 7.0 to 7.4, and a solution with a high content of proteins, preferably gelatin at 0.4%, weight by volume, with or without an effective quantity of a lipidic particles inducer agent, preferably with the effective quantity and the lipidic particles inducer agent used to form the antigen.

In a preferred embodiment, the effective quantity of the antigen suspension in the stage A it is of 50 to 100 $\mu$l. The second antibody can be also conjugated to the enzyme alkaline phosphatase, instead of peroxidase, in this case the corresponding alkaline phosphatase substrates are used.

In a specific embodiment, the hapten solution is obtained dissolving hapten in a buffer solution at pH between 7.0 and 7.4, in a relationship from 0.1 to 10 mmoles of hapten per liter of buffer solution.

In relation to the stabilization of membranes with drugs that avoid the formation of lipidic particles in liposomal model membranes or in cellular membranes, which in turn avoid the subsequent union of anti-lipidic particles antibodies, the studies were carried out with liposomal or cellular antigens using the cytofluorometry method. In a favorite modality this method includes the following steps:

A) A first step of incubation, in which the antigen suspension, liposomes or cells, are incubated with a drug that stabilizes its lipidic bilayers, this drug being used at a concentration of 0.1 up to 100 mM, the obtained mixture is incubated for 0.25 to 2 h at a temperature between 35 and 40° C.

B) A first step of addition and incubation, in which the antibody porter is added to the antigen stabilized with the stabilizer drug, this antibody porter is diluted from 1:5 up to 1:1000 into a buffer solution at pH between 7.0 to 7.4, and the resulting mixture is incubated for 0.25 to 2 h at a temperature between 35 and 40° C.

C) A first step of washing, in which the antigen stabilized with stabilizer drug and bound to the antibody porter is washed with a buffer solution at pH between 7.0 to 7.4, with or without an effective quantity of a lipidic particles inducer agent, preferably with the effective quantity of the inducer agent used to obtain the antigen.

D) A step of recovery, in which the antigen stabilized with stabilizer drug and bound to the antibody porter is recovered preferably by centrifugation.

E) A second step of addition and incubation, in which an effective quantity of a second antibody is added to the antigen stabilized with the stabilizer drug and bound to antibody porter. The resulting mixture is incubated for 0.25 to 2 h in the darkness at a temperature between 35 to 40° C. Second antibody is selected preferably among antibodies from a different specie to that of the antibody porter and they can be anti-Fc of human IgG, IgA and IgM or of the animal in study, or antibodies anti-Pc of IgM or of IgG depending on the nature of the monoclonal antibody when this is the antibody porter. Second antibody is used at a final dilution between 1:25 to 1:500 into a buffer solution at pH between 7.0 to 7.4, and it is conjugated to a substance or fluorescent substratum, preferably to FITC.

F) A second step of washing, in which the antigen stabilized with the stabilizer drug and bound to the antibody porter and the second antibody is washed with a buffer solution at pH between 7.0 to 7.4, with or without an effective quantity of a lipidic particles inducer agent, preferably with the same quantity and the same inducer agent used to obtain the antigen.

G) A step of suspension and analysis, in which the antigen stabilized with the stabilizer drug and bound to the antibody porter and the second antibody is suspended in a transporting solution, selected preferably between FACS Flow (Beckton Dickinson Co.) and Haema Line 2 (Serotono-Baker Diagnostics, INC) in a relationship from 1 to 5 mmole of the antigen in a liter of solution; this solution being preferably filtered previously with a 0.22 $\mu$m Millipore filter pore diameter, the obtained mixture being analyzed in a flow cytometer, preferably with a single 488 nm argon laser beam.

In a preferred embodiment, the antigen suspension is obtained suspending the antigen in a buffer solution at pH between 7.0 to 7.4, in a relationship of 1 to 5 mmole per liter of buffer solution for liposomal antigen. Furthermore, fluorescent substrate can also be selected from the group consisting of phycoerythrin, Cy3 and Percp.

This antigen is incubated with a drug that stabilizes its lipidic bilayers, this drug being used at a concentration of 0.1 up to 100 mM, the resulting mixture is incubated for 0.25 to 2 h at a temperature between 35 and 40° C.

In a specific embodiment the antigen can be a liposome suspension, or cells from human or animals.

The various aspects of the present invention, will be more clearly illustrated by the following examples, which are presented with illustrative purposes only and they should not be interpreted into a limitative form.

EXAMPLES

Liposomal antigens used in the examples were characterized by their $^{31}$p nuclear magnetic resonance spectra. These spectra showed lipids associated in bilayers or in lipidic particles in the liposomes as was previously described by Baeza et al. (op. cit., 1995), Aguilar (op. cit., 1997) and Aguilar et al., (op. cit., 1999).

Example 1

Indirect Detection by the Liposomal-ELISA Method of Lipidic Particles through the Detection of Anti-lipidic Particles Antibodies in Sera from Patients with the Antiphospholipid Syndrome Costar microtiter plates, with 96 flat-bottom wells with a high lipidic antigens binding property (Costar Co. Cambridge, USA), were coated by the addition of 100 $\mu$l per well of liposomes made from egg-yolk phosphatidylcholine:phosphatidate (2:1 mole ratio) in Tris-NaCl buffer (10 mM, 1 mM) pH 7, containing 0.1 $\mu$mol of phosphatidate, and treated with 5 mM $CaCl_2$ to induce lipidic particle formation. Microtiter plates were incubated 1 h at room temperature. After microtiter plates were incubated they were blocked for 1 h at room temperature by addition of 200 $\mu$l per well of 0.4% (w/v) gelatin in Tris-NaCl buffer (10 mM, 1 mM) pH 7, containing $CaCl_2$ 5 mM. Then the blocking solution was discarded by suction and 100 μl of human sera, from patients with the antiphospholipid syndrome, at 1:50 dilution using blocking solution were quickly added to each well in duplicate, to avoid that these wells becomes dry; all solutions were added subsequently in the same way. As a positive control, the supernatant of a hybridoma containing a monoclonal antibody against lipidic particles, from IgM isotype, at 1:100 dilution using blocking solution were added to four wells. Human sera were heated previously at 56° C. for 30 min for the inactivation of the complement. After microtiter plates were incubated 1 h at room temperature they were washed 4-times with 500 μl of blocking solution. Then 100 μl of peroxidase-conjugated goat anti-Fc of human IgG, IgA and IgM antibodies or anti-Fc of mouse IgM antibodies at 1:2000 dilution into blocking solution were added to each well, respectively, as second antibody. After 1 h of incubation at room temperature microtiter plates were washed 4-times again with the blocking solution and 100 μl of freshly prepared peroxidase substrates were added to each well (10 mg o-phenylenediamine, 25 ml Tris-NaCl buffer (10 mM, 1 mM) pH 7, and 20 μl of 30% $H_2O_2$) and allowed to incubate in an oven at 37° C. for 20 min. Enzyme reaction was stopped by addition of 50 μl per well of 2.5 M sulfuric acid. Absorbances were read at 492 nm in an ELISA Labsystems reader Multiskan MS model; duplicate values were averaged for each serum sample tested.

As negative controls the second antibody was added to wells in duplicate in the absence of human sera; in addition, human sera and the second antibody were added to wells in duplicate without liposomal antigens.

Results obtained by the liposomal-ELISA method were expressed in Arbitrary Units (AU) which are determined by the following equation:

$$AU = \frac{AsP - AsW}{AsH - AsW}$$

Where:

AsP=Absorbance at 492 nm of patients sera;

AsW=Absorbance at 492 nm of the control without human sera; and

AsH=Absorbance at 492 mn of healthy blood donators sera.

To determine the isotype of anti-lipidic particles antibodies, human sera that gave positive reaction were analyzed again but peroxidase-conjugated goat anti-Fc of human IgG or IgM antibodies were used as a second antibody; in order to determine whether the anti-lipidic particles antibodies correspond to the IgG or IgM isotype, respectively.

Analyzed Human Sera

Sera studied were obtained from the Bank of the Laboratory of Immunology of the Specialities Hospital of the Medical Center "LaRaza", from Mexico, D. F., México, and they came from thirty patients positive for anti-cardiolipin antibodies of the IgM or IgG isotype. Eleven patients meet with four or more of the American Rheumatism Association criteria for systemic lupus erythematosus (Tan et al., 1982, *Arthritis Rheum.* 25:1271–1277), twelve meet with the criteria for the primary antiphospholipid syndrome (Asherson et al., op. cit., 1996; Piette et al., 1993, *J. Rheumatol.* 20:1802–1804), and seven for the antiphospholipid syndrome secondary to systemic lupus erythematosus (Asherson et al., op. cit., 1996) (Table 1).

Anti-cardiolipin antibodies were detected using cardiolipin coated to ELISA microtiter plates as antigen (Loizou et al., 1985, *Clin. Exp. Immunol.* 62:738–745). Results are also expressed in Arbitrary Units (AU) and they are considered positive when they have values $\geq 1.9$ AU for IgG isotype, and $\geq 2.4$ AU for IgM isotype (Loizou et al., op. cit., 1985). All patients' sera were positive for IgG isotype and some of them were positive for IgM isotype (Table 2).

TABLE 1

Criteria for the classification of primary antiphospholipid syndrome, systemic lupus erythematosus, and antiphospholipid syndrome secondary to systemic lupus erythematosus from the American Rheumatism Association.

| Systemic lupus erythematosus | Primary antiphospholipid syndrome | Antiphospholipid syndrome secondary to systemic lupus erythematosus |
|---|---|---|
| Serositis: | Venous and arterial thrombosis: | Malar rash |
| -Pleuritis | -Renal complications | Discoid rash |
| -Pericarditis | -Pulmonary embolism | Oral or pharyngeal ulceration |
|  | -Cerebral ischemia | Frank arthritis |
|  | -Necrotic skin ulcerations |  |
|  | -Myocardial infarction with uremia |  |
| Nephropathy | Nervous system complications: | Persistent proteinuria greater |
|  | -Stroke and transient attack | than 0.5 g/day |
|  | -Neurological disorders |  |
| Neurologic disorders: | Haematological disorders: | -Pleuritis, in the absence of |
| -Seizures | -Thrombocytopenia | pulmonary embolism. |
| -Psychosis | -Haemolytic anaemia | -Pericarditis, in the absence of myocardial infarction or uremia |
| Haematological disorders: | Antiphospholipid antibodies: | Antibodies to native DNA |
|  | -Anti-cardiolipin | Antiphospholipid antibodies |

TABLE 1-continued

Criteria for the classification of primary antiphospholipid syndrome, systemic lupus erythematosus, and antiphospholipid syndrome secondary to systemic lupus erythematosus from the American Rheumatism Association.

| Systemic lupus erythematosus | Primary antiphospholipid syndrome | Antiphospholipid syndrome secondary to systemic lupus erythematosus |
|---|---|---|
| -Thrombocytopenia<br>-Haemolytic anaemia | -Lupus anticoagulant<br>-Anti-phosphatidylethanolamine<br>-Anti-phosphatidylserine | Anti-$\beta_2$-glycoprotein I antibodies |
| Immunologic disorders:<br>-False positive VDRL<br>-Antibodies to dsDNA<br>-Antinuclear antibodies | Anti-$\beta_2$-glycoprotein I antibodies | Venous and arterial thrombosis:<br>-Renal complications<br>-Pulmonary embolism<br>-Cerebral ischemia<br>-Necrotic skin ulcerations<br>-Myocardial infarction with uremia |
|  | Recurrent fetal loss | Lymphopenia less that 1000/$\mu$l<br>Recurrent fetal loss |

TABLE 2

Detection of anti-cardiolipin and anti-lipidic particles antibodies in human sera

| Healthy blood donors | Anti-cardiolipin Antibodies (ELISA) IgM (+) ≧ 2.4 AU | Anti-cardiolipin Antibodies (ELISA) IgG (+) ≧ 1.9 AU | Anti-lipidic particles Antibodies (liposomal antigen made from phosphatidylcholine: phosphatidate (2:1) + CaCl$_2$) (Cytofluorometry) Positive results at: (+) D ≧ 0.5, p < 0.001 (Polyvalent) | Patients' sera and diagnostic | | Anti-cardiolipin antibodies (ELISA) IgM (+) ≧ 2.4 AU | Anti-cardiolipin antibodies (ELISA) IgG (+) ≧ 1.9 AU | Anti-lipidic particles antibodies (liposomal antigen made from phosphatidylcholine: phosphatidate (2:1) + CaCl$_2$) (Cytofluorometry) Positive results at: (+) D ≧ 0.5, p < 0.001 Polyvalent | IgM | IgG |
|---|---|---|---|---|---|---|---|---|---|---|
| 1H | — | — | — | AC11 | PAPS | — | 7.5 | D = 0.76 | — | D = 0.54 |
| 2H | — | — | — | AC12 | PAPS | — | 56.3 | D = 0.77 | — | D = 0.70 |
| 3H | — | — | — | AC13 | SLE | 5.24 | 17.2 | D = .77 | D = 0.65 | D = 0.70 |
| 4H | — | — | — | AC14 | SLE | — | 10.6 | D = 0.74 | D = 0.65 | D = 0.62 |
| 5H | — | — | — | AC15 | PAPS | — | 6.7 | D = 0.74 | D = 0.50 | D = 0.84 |
| 6H | — | — | — | AC16 | SLE | — | 2.52 | D = 0.75 | D = 0.56 | D = 0.59 |
| 7H | — | — | — | AC17 | SLE | — | 4.3 | D = 0.75 | — | D = 0.59 |
| 8H | — | — | — | AC18 | SLE + APS | — | 67.4 | D = 0.73 | — | D = 0.63 |
| 9H | — | — | — | AC19 | SLE | — | 13.6 | D = 0.73 | D = 0.72 | D = 0.73 |
| 10H | — | — | — | AC20 | SLE | — | 9.3 | D = 0.75 | D = 0.52 | D = 0.73 |
| 11H | — | — | — | AC21 | PAPS | — | 3.36 | D = 0.75 | — | D = 0.62 |
| 12H | — | — | — | AC22 | SLE + APS | 2.8 | 15.4 | D = 0.56 | D = 0.52 | D = 0.61 |
| 13H | — | — | — | AC23 | SLE + APS | — | 19.2 | D = 0.59 | — | D = 0.61 |
| 14H | — | — | — | AC24 | PAPS | — | 18.0 | D = 0.61 | — | D = 0.61 |
| 15H | — | — | — | AC25 | PAPS | 3.95 | 16.3 | D = 0.53 | — | D = 0.62 |
| 16H | — | — | — | AC26 | SLE | 3.06 | 9.2 | D = 0.53 | — | D = 0.62 |
| 17H | — | — | — | AC27 | PAPS | — | 8.6 | D = 0.51 | — | D = 0.54 |
| 18H | — | — | — | AC28 | PAPS | — | 11.5 | D = 0.51 | — | D = 0.54 |
| 19H | — | — | — | AC29 | SLE | — | 11.08 | D = 0.43 | D = 0.52 | D = 0.57 |
| 20H | — | — | — | AC30 | PAPS | — | 14.7 | N/D | D = 0.52 | D = 0.57 |
| 21H | — | — | — | AC31 | SLE + APS | — | 19.4 | D = 0.66 | D = 0.66 | D = 0.50 |
| 22H | — | — | — | AC32 | SLE + APS | 3.0 | 39.6 | D = 0.56 | — | D = 0.57 |
| 23H | — | — | — | AC33 | PAPS | — | 23.7 | D = 0.56 | — | D = 0.54 |
| 24H | — | — | — | AC34 | SLE + APS | — | 34.4 | D = 0.56 | — | D = 0.74 |
| 25H | — | — | — | AC35 | PAPS | 4.0 | 18.0 | D = 0.66 | D = 0.56 | D = 0.75 |
| 26H | — | — | — | AC36 | SLE | 44.0 | 158.0 | D = 0.64 | D = 0.60 | D = 0.64 |
| 27H | — | — | — | AC37 | SLE | — | 11.0 | D = 0.64 | D = 0.70 | D = 0.75 |
| 28H | — | — | — | AC38 | PAPS | 3.0 | 2.0 | D = 0.64 | D = 0.59 | D = 0.75 |
| 29H | — | — | — | AC39 | SLE + APS | — | 52.0 | D = 0.64 | D = 0.76 | D = 0.75 |
| 30H | — | — | — | AC40 | SLE | 4.0 | 18.0 | D = 0.66 | D = 0.56 | D = 0.75 |

PAPS.- Primary antiphospholipid syndrome.
SLE.- Systemic lupus erythematosus.
APS + SLE.- Antiphospholipid syndrome secondary to systemic lupus erythematosus Sera from healthy blood donors, in other words, of healthy subjects which were used as negative controls in the analyzed immunoreactions, did not show anti-cardiolipin antibodies from IgM or IgG isotype (Table 2). These sera came from the Bank of Blood of the Medical Center "La Raza", from México, D. F., México.

Patients' sera and sera from helathy blood donators were supplied us by Dr. Carlos Lavalle Montalvo, Manager of the Infectology Hospital of the Medical Center "La Raza", from México, F. F., México.

Results of the Detection by the Liposomal-ELISA Method of Anti-lipidic Particles Antibodies in Human Sera Reaction of human sera, from healthy blood donators or from patients with the antiphospholipid syndrome, with liposomal antigens made from egg-yolk phosphatidylcholine:phosphatidate (2:1 mole ratio) in Tris-NaCl buffer (10 mM, 1 mM) pH 7, containing 0.1 µmol of phosphatidate, and treated with 5 mM $CaCl_2$ to induce lipidic particles formation, is showed in FIG. 1. Immunoreaction of patients sera with the lipidic particles was clearly different from that of healthy blood donators sera, or control sera, since the reaction with the peroxidase substrates was negative when control sera were used. In general, control serum gave values smaller than one AU. All the values from control sera were combined to obtain the arithmetic mean and the standard deviation. We then consider as positive all results greater than 3 standard deviations from the mean. After this analysis, sera from the 30 healthy blood donors were mixed and the mixture was used as a control sera for subsequent analysis. In FIG. 1 the dark line indicates the upper limit above which the reactions of sera with lipidic antigens are positive. The reaction of most patients sera was clearly positive, with values of AU higher than 6.

Arbitrary Units of 7 sera (AC12, AC14, AC15, AC16, AC31, AC32 and AC34) are showed in FIG. 1. These sera are representative of the 30 analyzed sera. AC12 and AC15 sera correspond to patients with primary antiphospholipid syndrome (PAPS); AC14 and AC16 sera from patients with systemic lupus erythematosus (SLE) and AC31, AC32, and AC34 sera from patients with antiphospholipid syndrome secondary to systemic lupus erythematosus (APS+SLE). In this Figure as a positive control it is showed the reaction of H308 monoclonal antibody with liposomal antigens from egg-yolk phosphatidylcholine:phosphatidate (2:1 mole ratio) in Tris-NaCl buffer (10 mM, 1 mM) pH 7, containing 0.1 µmol of phosphatidate, and treated with 5 mM $CaCl_2$ to induce lipidic particles formation. Peroxidase-conjugated goat anti-Fc of human IgG antibodies were used as second antibody for the human sera and anti-Fc of mouse IgM for monoclonal antibody, both at 1:2000 final dilution.

An important particularity of liposomal-ELISA method consists in that it allows the simultaneous determination of anti-lipidic particles antibodies in at least 40 sera samples by microtiter plate, each one in duplicate; for this reason this method can be easily applied to the diagnosis of illnesses where this type of antibodies is presented.

Example 1A

Comparative Study when Antigens without Lipidic Particles and Sera from Patients with the Antiphospholipid Syndrome Are Used in the Liposomal-ELISA Method Example 1 was repeated but using as antigens "rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, which when incubated with 5 mM $BaCl_2$ they conserve the smooth surface of bilayer. In this case, the reaction of the substrates of peroxidase-conjugated to the second antibody was negative. Because liposomes did not have any lipidic particles, therefore the anti-lipidic particles antibodies did not react with them and consequently the second antibody did not bind these liposomes, which explains the negative reaction of peroxidase substrates. These results discard the possibility that anti-lipidic particles antibodies recognize a lipid-divalent cation complex and/or the reduction in the liposomal surface charge due to the binding of divalent cations without affecting the bilayer lipid arrangements and their change to lipidic particles arrangements (Aguilar et al., op. cit., 1999).

Example 1B

Comparative Study when Antibodies Different to the Anti-lipidic Particles Antibodies and Liposomal Antigens Bearing Lipidic Particles Are Used in the Liposomal-ELISA Method Example 1 was repeated with some modifications. In this experiment liposomes made from egg yolk phosphatidylcholine:phosphatidate (2:1 mole ratio) in Tris-NaCl buffer (10 mM, 1 mM) pH 7, containing 0.1 µmol of phosphatidate, and treated with 5 mM $CaCl_2$ to induce lipidic particles formation, were incubated directly with peroxidase-conjugated goat anti-Fc of human IgG, IgA and IgM antibodies, or with the supernatant of a hybridoma producing unrelated monoclonal antibodies, as those against a membranal protein of *Trichinella spiralis*, from IgM isotype, and peroxidase-conjugated goat anti-Fc of mouse IgM antibodies. In both cases, the reaction with peroxidase substrates was negative, because in absence of human anti-lipidic particles antibodies or mouse anti-lipidic particles monoclonal antibody the second antibody, peroxidase-conjugated goat anti-Fc of human IgG, IgA and IgM or anti-Fc of mouse IgM antibodies, do not bind directly to lipidic particles induced by calcium in liposomal antigens.

Example 1C

Comparative Study when Anti-lipidic Particles Antibodies and Second Antibody Are Used in Absence of Liposomal Antigens Bearing Lipidic Particles in the Liposomal-ELISA Method Example 1 was repeated but in the absence of liposomal antigens, in consequence the reaction of substrates of the peroxidase-conjugated to second antibody was negative. Due to anti-lipidic particles antibodies do not bind directly to microtiter plate which could give a false positive result, because microtiter plate was blocked with the gelatin that is used in this methodology, consequently the second antibody do not bind to microtiter plate which explains the negative reaction of the substrates of peroxidase-conjugated to the second antibody.

From these examples we can conclude that, in a preferred embodiment of the present invention, a diagnosis kit particularly useful for the detection by the protocol of liposomal-ELISA of anti-lipidic particles antibodies in at least a serum sample from a subject suffering from an illnesses related with antiphospholipid antibodies include: an indicator reagent including, firstly, at least liposomes with lipidic particles and, secondly, at least an anti-lipidic particles monoclonal antibody; at least a blocking solution to prevent possible false positive results from occurring; at least a buffer solution, as a medium to allow the reaction between the sample coming from the sick person with this indicator reagent to proceed; enzymatic media that include preferably the peroxidase enzyme, to make evident this reaction; and at least a sample of a reference serum coming from a healthy individual, as negative control of the reaction with liposomal antigens bearing lipidic particles.

In this preferred embodiment of the diagnosis kit, the serum sample coming from the ill subject is made react with the indicator reagent containing liposomes bearing lipidic particles. Also, the indicator reagent containing liposomes with lipidic particles is made react with the anti-lipidic particles monoclonal antibody, as a positive control, showing that the system to detect the reaction between anti-lipidic particles antibodies from the serum of a subject suffering from an illnesses associated with antiphospholipid antibodies and the antigen bearing lipidic particles works correctly.

In an alternative embodiment, the diagnosis kit also comprises as some part of it one or more microtiter plate(s) as recipient(s) for the development of the reaction. In the same fashion, in another alternative modality the sample of a healthy individual serum can not be included in the same kit, being obtained, in this case, from an external source. This serum sample is coming from a healthy individual who does not present an illness associated with antiphospholipid antibodies.

Example 2

Detection by Cytofluorometry of the Liposomal Antigens Autofluorescence

Samples of 100 μl of liposomes made from egg yolk phosphatidylcholine:phosphatidate (2:1 mole ratio) in Tris-NaCl buffer (10 mM, 1 mM) pH 7, containing 0.1 μmol of phosphatidate were analyzed in a FACSCalibur Flow Cytometer equipped with a single 488 nm argon laser beam (Beckton Dickinson). Autofluorescence readings were obtained from 10,000 liposomes in a logarithmic mode and they were made in the FL-1 channel at 748 V (Baeza et al., op. cit. 1995). The obtained data were analyzed with the Cellquest program (Beckton Dickinson).

Figure 2:
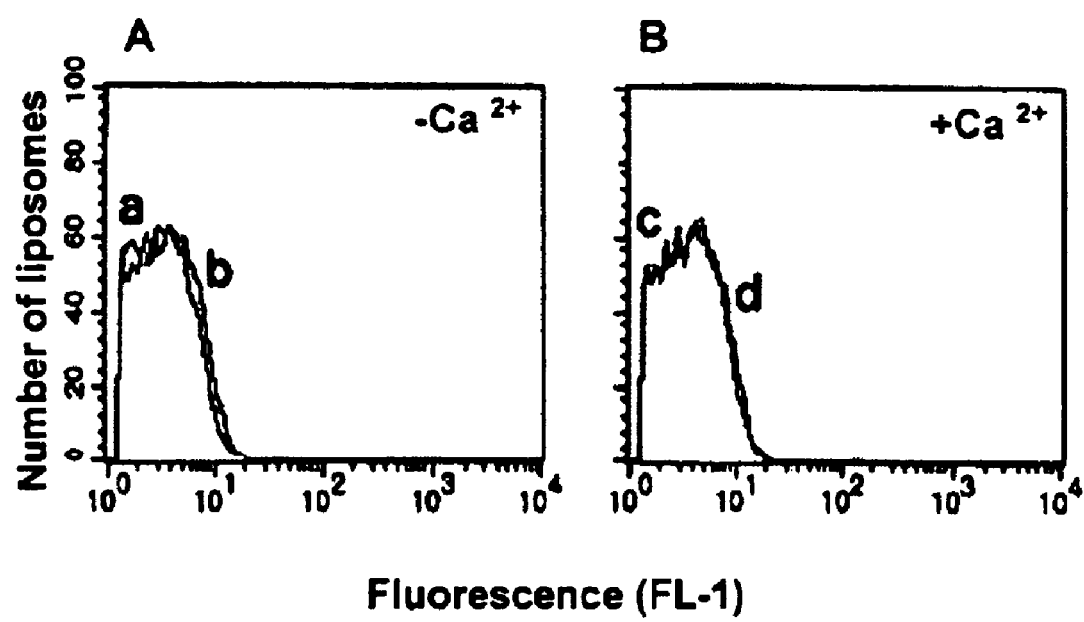
FIGS. 2A and 2B illustrate the fluorescence graphs of liposomes made from PC:PA (2:1 mole ratio), with and without lipidic particles induced by calcium, that were incubated with Tris-NaCl (10 mM, 1 mM) pH 7, or with the second antibody conjugated to peroxidase.

Autofluorescence histograms obtained from egg yolk phosphatidylcholine: phosphatidate (2:1 mole ratio) liposomes showed values between 1 to 10 fluorescence units (a, FIG. 2A). The detection of liposomal autofluorescence allowed the application of cytofluorometry to the analysis of immunologic reactions where liposomal antigens are used. Liposomal autofluorescence (a, FIG. 2A) was not modified when liposomes were incubated with 5 mM $CaCl_2$ (c, FIG. 2B), which indicates that the presence of lipidic particles in liposomes did not modify the liposomal autofluorescence. Furthermore, this fluorescence was not modified by the addition of FITC-conjugated goat anti-Fc of human IgG, IgA and IgM or anti-Fc of mouse IgM antibodies as second antibodies, which indicates that these antibodies do not bind directly liposomal antigens, and therefore they can not produce a false positive reaction. Results with the FITC-conjugated goat anti-Fc of human IgG, IgA and IgM antibodies as second antibody at 1:200 final dilution are shown in: b, FIG. 2A and d, FIG. 2B, with liposomal antigens in absence of calcium (b, FIG. 2A) as in presence of this divalent cation (d, FIG. 2B).

Similar results were obtained with liposomes made from phosphatidylcholine; phosphatidylcholine:cardiolipin (2:1 mole ratio); phosphatidylcholine:phosphatidylserine (4:1 mole ratio) or from dipalmitoylphosphatidylcholine:egg-yolk phosphatidylcholine:dipalmitoylphosphatidate (1.2:0.8:1 mole ratio), respectively. Therefore the cytofluorometry can be applied in general to the analysis of immunologic reactions where liposomal antigens with different lipidic formulations are used.

Example 2A

Detection by the Liposomal Cytofluorometry Method of Lipidic Particles in Liposomes Using H308 Monoclonal Antibody Samples of 100 μl of liposomes made from egg yolk phosphatidylcholine:phosphatidate (2:1 mole ratio) in Tris-NaCl buffer (10 mM, 1 mM) pH 7, containing 0.1 μmol of phosphatidate, and treated with 5 mM $CaCl_2$ to induce lipidic particles formation, were placed in 14×95 mm ultra-centrifuge tubes (Beckman ultra-clear No. 344060). To each one of these aliquots the supernatant of a hybridoma, the H308, that generates an anti-lipidic particles monoclonal antibody at 1:100 final dilution into Tris-NaCl buffer (10 mM, 1 mM) pH 7, was added. After incubation for 1 h at 37° C., liposomes were washed with 12 ml of Tris-NaCl buffer (10 mM, 1 mM) pH 7, containing 5 mM $CaCl_2$. Liposomes were recovered by centrifugation in the ultracentrifuge Beckman L8-M, at 202,000×g for 50 min at 18° C. Next FITC-conjugated goat anti-Fc of mouse IgM antibodies at 1:200 final dilution into Tris-NaCl buffer (10 mM, 1 mM) pH 7, was added to each tube as second antibody and was incubated 1 h at 37° C. in the darkness. At the end of the incubation liposomes were washed as it was previously indicated. Finally, liposomes preparation were resuspended in 500 μl of FACS flow solution (Beckton Dickinson Co.) filtered with a 0.22 μm Millipore filter pore diameter. This liposomal suspension was analyzed by cytofluorometry in a FACSCalibur Flow Cytometer equipped with a single 488 nm argon laser beam (Beckton Dickinson).

Fluorescence readings were made in the FL-1 channel. The relative size and/or liposomal aggregation were analyzed by diffraction of the laser beam in the FSC (forward scatter light) channel and the granularity or liposomal bilayers complexity was analyzed be refraction and reflection of the laser in the SSC (side scatter light) channel. Analysis of 10,000 liposomes was made in a logarithmic scale with the following detectors: FSC in E00, with a detector compensation threshold of 52 V; SSC of 401 V and FL-1 of 748 V (Baeza et al., op. cit., 1995). The obtained data were analyzed with the Cellquest program (Beckton Dickinson).

"Rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, alone or incubated with $BaCl_2$ 5 mM were also used as antigens.

Figure 3:
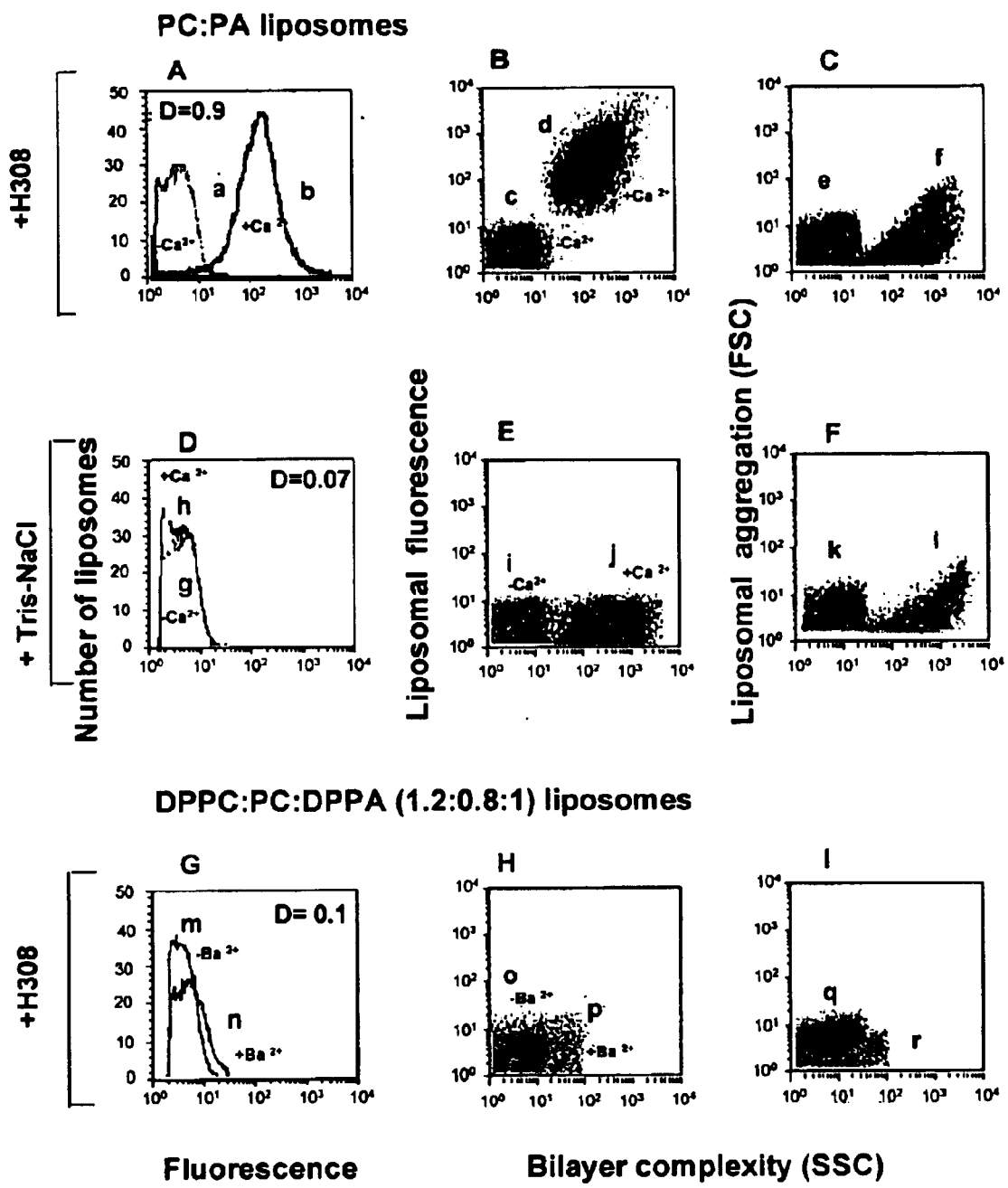
FIGS. 3A–3I show the cytofluorometric analysis of the reaction between H308 monoclonal antibody and liposomal antigens made from PC:PA (2:1 mole ratio) or from dipalmitoylphosphatidylcholine:egg-yolk phosphatidylcholine:dipalmitoylphosphatidate [DPPC:PC:DPPA] (1.2:0.8:1 mole ratio). As well as the cytofluorometric analysis of liposomal antigens from PC:PA (2:1 mole ratio) in Tris-NaCl (10 mM, 1 mM), with or without lipidic particles induced by calcium, in absence of the H308 monoclonal antibody.

H308 monoclonal antibody do not show any reactivity with bilayer lipid arrangements, since the fluorescence detected from smooth liposomes incubated with this monoclonal antibody (a, FIG. 3A) was similar to the autofluorescence of control liposomes, in Tris-NaCl or treated with calcium, that were not incubated with monoclonal antibody (g, h, FIG. 3D). Furthermore, SSC and FSC values indicated the absence of lipidic particles and of liposomal aggregation in smooth liposomes that were not treated with calcium (i, FIG. 3E; k, FIG. 3F) no matter if they were incubated with H308 monoclonal antibody (c, FIG. 3B; e, FIG. 3C). On the contrary, the 60-fold increase in the fluorescence of liposomes treated with calcium (b, FIG. 3A) with regard to the fluorescence of liposomes with lipids in bilayers (a, FIG. 3A), with a value in the fluorescence difference among these liposomal populations in a logarithmic scale (D)=0.9 at p<0.001, showed the reaction of H308 monoclonal antibody with the lipidic particles induced by calcium. Values of D≧0.5 at p<0.001 indicate a difference among the studied populations that is highly significant from the statistical point of view (Lampariello, 2000, Cytometry 39:179–188). Therefore, values of D≧0.5 at p<0.001 were considered as positive results and indicative of the presence of anti-lipidic particles antibodies in the analyzed samples.

On the other hand, SSC values indicated that the pattern of lipidic particles was different after the immunoreaction (d, FIG. 3B) compared with the pattern of these lipidic structures in liposomes that were not incubated with H308 monoclonal antibody (j, FIG. 3E); these profiles reflect the dynamic properties of lipidic particles. Besides, liposomal aggregation, was discarded, because FSC values that show liposomal aggregation, were similar after the immunoreaction (f, FIG. 3C) to those of liposomes with lipidic particles that were not incubated with H308 monoclonal antibody (l, FIG. 3F).

Monoclonal antibody reaction with lipidic particles of liposomal antigens is considered as a positive reference of the reaction of patients' antibodies with this type of lipidic structures. In consequence it is necessary to include this determination as a positive control in the analysis of the detection of anti-lipidic particles antibodies in sera from human individuals or animals by liposomal cytofluorometry.

On the other hand, a monoclonal antibody, from isotype IgM, unrelated with the liposomal system analyzed, as the one directed against a membranal protein of *Trichinella spiralis*, did not show the indicate reactions for H308 monoclonal antibody with lipidic particles. Since cytofluorometry graphs obtained with this unrelated monoclonal antibody were similar to those of control liposomes treated with calcium in absence of H308 monoclonal antibody (h, FIG. 3D; j, FIG. 3E; and l, FIG. 3F).

"Rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, that incubated with 5 mM $BaCl_2$ conserved the smooth surface of bilayers did not show any reaction with H308 monoclonal antibody, because the cytofluorometry graphs obtained (n, FIG. 3G; p, FIG. 3H; and r, FIG. 3I) were similar to those of liposomes that were not treated with $BaCl_2$ neither with the monoclonal antibody (m, FIG. 3G; o, FIG. 3H; and q, FIG. 3I).

Example 2B

Indirect Detection by the Liposomal Cytofluorometry Method of Lipidic Particles through the Detection of Anti-lipidic Particles Antibodies in Sera from Patients with the Antiphospholipid Syndrome This detection is similar to the one described in Example 2A, however sera from patients with antiphospholipid syndrome were used as the antibody carrier instead of H308 monoclonal antibody. Samples of 100 µl of liposomes made from egg yolk phosphatidylcholine:phosphatidate (2:1 mole ratio) in Tris-NaCl buffer (10 mM, 1 mM) pH 7, containing 0.1 µmol of phosphatidate, and treated with 5 mM $CaCl_2$ to induce lipidic particles formation were placed in 14×95 mm ultracentrifuge tubes (Beckman ultra-clear No. 344060). Sera from patients with the antiphospholipid syndrome at 1:50 final dilution into Tris-NaCl buffer (10 mM, 1 mM) pH 7, were added to each one of ultracentrifuge tubes and they were incubated for 1 h at 37° C. Sera were previously heated at 56° C. for 30 min for the inactivation of the complement. After incubation, liposomes were washed with 12 ml of Tris-NaCl buffer (10 mM, 1 mM) pH 7, containing 5 mM $CaCl_2$. Liposomes were recovered by centrifugation in the ultracentrifuge Beckman L8-M, at 202,000×g for 50 min at 1 8° C. Next it was added to each tube FITC-conjugated goat anti-Fc of human IgG, IgA and IgM antibodies at 1:200 final dilution into Tris-NaCl buffer (10 mM, 1 mM) pH 7, as second antibody and was incubated 1 h at 37° C. in the darkness. At the end of incubation liposomes were washed as it was previously indicated. Finally, liposome preparations were resuspended in 500 µl of FACS flow solution (Beckton Dickinson Co.) filtered with a 0.22 µm Millipore filter pore diameter. This liposomal suspension was analyzed by cytofluorometry in a FACSCalibur Flow Cytometer equipped with a single 488 nm argon laser beam (Beckton Dickinson).

Fluorescence readings were made in the FL-1 channel. The relative size and/or liposomal aggregation were analyzed in the FSC channel and the granularity or liposomal bilayers complexity was analyzed in the SSC channel. Analysis of 10,000 liposomes was made in a logarithmic mode with the following detectors: FSC in E00, with a detector compensation threshold of 52 V; SSC of 401 V and FL-1 of 748 V (Baeza et al., op. cit., 1995). The obtained data were analyzed with the Cellquest program (Beckton Dickinson).

As a negative control, the reaction of healthy blood donors sera with liposomes made from egg yolk phosphatidylcholine:phosphatidate (2:1 mole ratio) in Tris-NaCl buffer (10 mM, 1 mM) pH 7, containing 0.1 µmol of phosphatidate, and treated with 5 mM $CaCl_2$ to induce lipidic particles formation was analyzed. FITC-conjugated goat anti-Fc of human IgG, IgA and IgM antibodies were used as second antibody.

Figure 4:
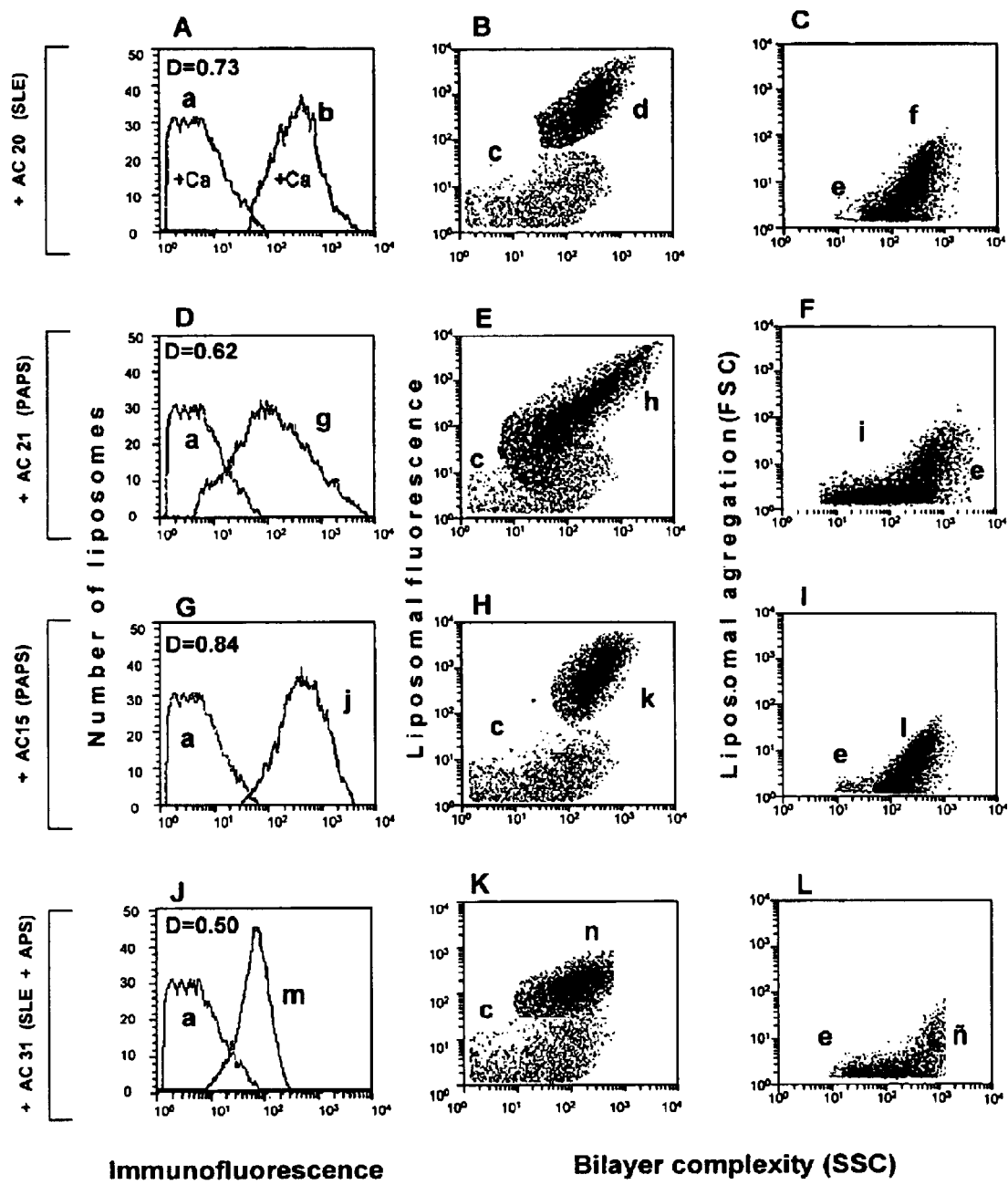
FIGS. 4A–4X show the cytofluorometric analysis of the reaction between sera from human healthy blood donators or from patients with the antiphospholipid syndrome, and liposomal antigens made from PC:PA (2:1 mole ratio) bearing lipidic particles induced by calcium.
Figure 4:
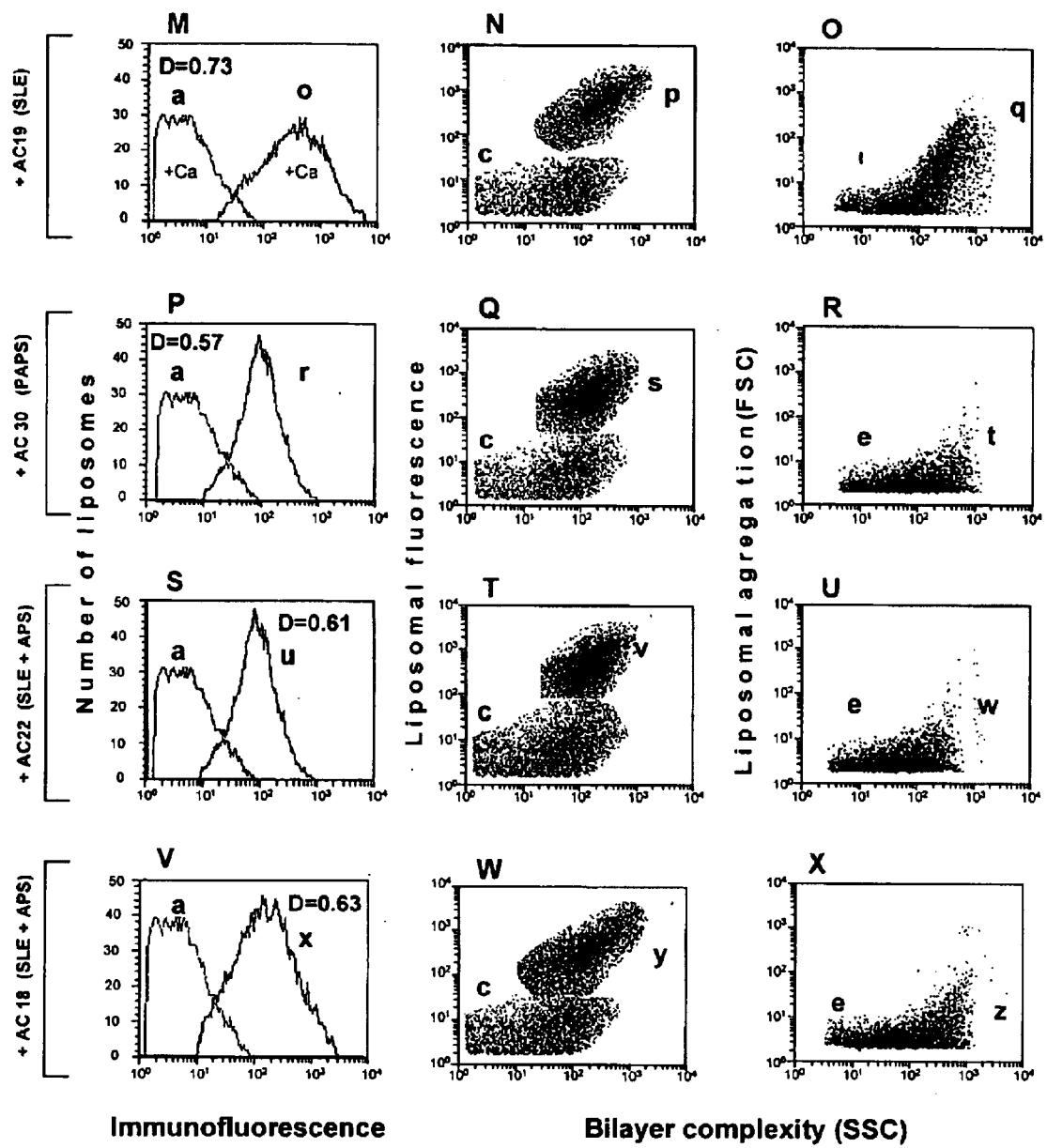

Thirty healthy blood donors' sera were studied. These sera did not present any immunoreaction with lipidic particles, since fluorescence graphs obtained with liposomes incubated with them were similar to those of control liposomes that were exclusively incubated with 5 mM $CaCl_2$ (h, FIG. 3D; and j, FIG. 3E from Example 2A). After this analysis, sera from the 30 healthy blood donors were mixed and the mixture was used as a control sera for subsequent analysis. Cytofluorometry graphs of mixed sera are presented in: a, FIGS. 4A, D, G, J, M, P, S and V; in c, FIGS. 4B, E, H, K, N, Q, T and W, and in e, FIGS. 4C, F, I, L, O, R, U and X. FSC values (e, FIGS. 4C, F, I, L, O, R, U and X) showed the absence of liposomal aggregation by the treatment with healthy blood donators sera, because they were very similar to those of liposomes control in absence of human sera indicated in: 1, FIG. 3F, from Example 2A.

Immunoreaction of all patients' sera with liposomal antigens treated with calcium showed a fluorescence 20 to 40-fold higher than that of control sera reaction, with a difference between liposomal fluorescence in a logarithmic scale (D)$\geq$0.5 at p<0.001 (Table 2). Values of D$\geq$0.5 at p<0.001 were considered as positive results and indicative of the presence of anti-lipidic particle antibodies in sera analyzed, in a similar way as it was described for H308 monoclonal antibodies. As example, fluorescence histograms of eight sera from patients with systemic lupus erythematosus (SLE) (AC19 and AC20), with primary antiphospholipid syndrome (PAPS) (AC15, AC21 and AC30) or with antiphospholipid syndrome secondary to systemic lupus erythematosus (SLE+APS) (AC18, AC22 and AC31) are shown in: b, FIG. 4A; g, FIG. 4D; j, FIG. 4G; m, FIG. 4J; o, FIG. 4M; r, FIG. 4P; u, FIG. 4S; and x, FIG. 4V. In the eight sera the reaction between anti-lipidic particle antibodies contained in patients' sera and lipidic particles of liposomal antigens although positive, were clearly different from each other and with regard to the reaction of H308 monoclonal antibody (compare d, FIG. 4B; h, FIG. 4E; k, FIG. 4H; n, FIG. 4K; p, FIG. 4N; s, FIG. 4Q; v, FIG. 4T; and y, FIG. 4W with d, FIG. 3B, from Example 2A), which can be attributed to the polyclonal origin of human antibodies.

SSC values (d, FIG. 4B; h, FIG. 4E; k, FIG. 4H; n, FIG. 4K; p, FIG. 4N; s, FIG. 4Q; v, FIG. 4T; and y, FIG. 4W), parameter where liposomal bilayer complexity and therefore the presence of lipids associated in lipidic particles is analyzed, were similar to those of control liposomes incubated with calcium to induce lipidic particles formation (j, FIG. 3E, from Example 2A). Therefore, SSC values showed the presence of lipidic particles in liposomes which gave the reaction with the anti-lipidic particles antibodies contained in patients sera.

Furthermore, the reaction of patients sera with lipidic particles did not show any liposomal aggregation, that could increase in an unspecific form the fluorescence registered and to give a positive false result, since FSC values (f, FIG. 4C; i, FIG. 4F; l, FIG. 4I; n, FIG. 4L; q, FIG. 4O; t, FIG. 4R; w, FIG. 4U; and z, FIG. 4X) were similar after the immunoreaction to those of liposomes incubated with healthy blood donators sera (e, FIGS. 4C, F, I, L, O, R, U and X) and with those incubated with calcium in absence of antibodies (l, FIG. 3F, from Example 2A).

Since liposomal cytofluorometry method has a sensibility 10-fold higher than liposomal-ELISA method in the detection of anti-lipidic particles antibodies it must be applied when some doubtful result has been obtained with liposomal-ELISA method. For example, sera such as AC27 that show by liposomal-ELISA method a value of AU<1.0, which is negative for the detection of anti-lipidic particles antibodies, by liposomal cytofluorometry it shows a result with a value of D=0.51, at p<0.001, which is clearly positive of the presence of anti-lipidic particles antibodies.

Example 2C

Comparative Study when Liposomal Antigens without Lipidic Particles and Sera from Patients with the Antiphospholipid Syndrome Are Used in the Cytofluorometry Method "Rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, that incubated with $BaCl_2$ 5 mM conserved the smooth surface, were used as antigens. In "rigid" liposomes there were not the formation of lipidic particles because their rigid bilayers do not allow the lipidic movement that is required to form lipidic particles. These liposomes were incubated with sera from patients with the antiphospholipid syndrome and FITC-conjugated goat anti-Fc of human IgG, IgA and IgM antibodies were used at a final dilution of 1:200 as second antibody.

Figure 5:
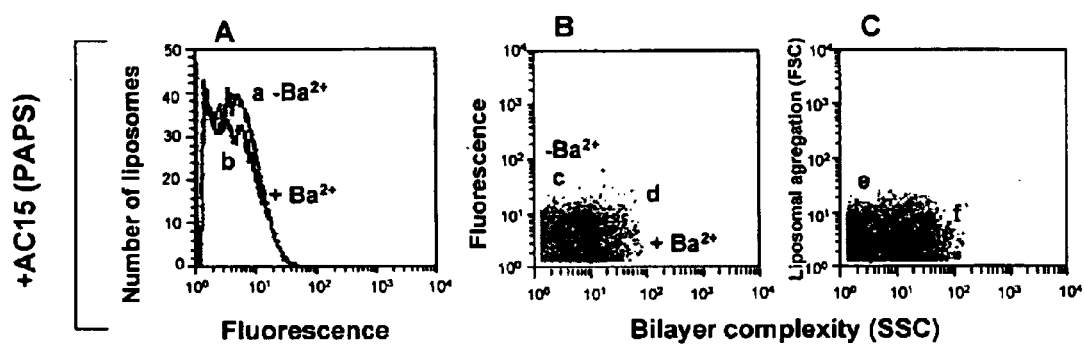
FIGS. 5A–5C show the cytofluorometric analysis which indicate that the AC15 serum from a patient with primary antiphospholipid syndrome does not show any immunoreaction with liposomal antigens made from DPPC:PC:DPPA (1.2:0.8:1 mole ratio) that lack lipidic particles.

Cytofluorometry graphs obtained showed that patients sera did not present any reaction with "rigid" liposomes treated with $BaCl_2$ (b, FIG. 5A; d, FIG. 5B; and f, FIG. 5C) because they were similar to those of liposomes that were not treated with $BasCl_2$ (a, FIG. 5A; c, FIG. 5B; and e, FIG. 5C). Graphs showed in FIGS. 5A–5C, correspond to the reaction of AC15 serum from a patient with primary antiphospholipid syndrome (PAPS) and it is representative of reaction of sera from the remaining patients indicated in Table 2.

From the above mentioned examples, we can conclude that in another favorite modality of the present invention, a diagnosis kit particularly useful for the detection by the liposomal cytofluorometry method of anti-lipidic particles antibodies in sera from subjects with illnesses associated with antiphospholipid antibodies comprises: an indicator reagent, including at least liposomes bearing lipidic particles; at least a buffer solution as medium to allow the reaction between the ill subject sample with this indicator reagent to proceed; and fluorescent media to make evident this reaction.

In this preferred embodiment of the diagnosis kit, sera sample coming from ill subjects is made react with the indicator reagent containing liposomes bearing lipidic particles.

In an alternative embodiment, the diagnosis kit includes as some part of it one or more tube(s) for centrifugation as recipient(s) for the development of the reaction.

In the same fashion, in another alternative embodiment this diagnosis kit can include at least an anti-lipidic particles monoclonal.antibody as a positive control of the antibodies reaction with liposomal antigens bearing lipidic particles, and at least a sample of a reference serum coming from a healthy individual, as a negative control of the reaction with liposomal antigens bearing lipidic particles.

In another alternative embodiment the serum sample of a healthy individual can be obtained from an external source. This serum sample is coming from a healthy individual that does not present an illness associated with antiphospholipid antibodies.

Example 3

Direct Detection by the Immunofluorescence Method of Lipidic Particles in Cells from a Subject Using H308 Monoclonal Antibody C5337 cancer pancreas cells were used as antigens. In a cellular culture plate, with 24-wells containing sterile micro cover glasses in each one of the wells, $1 \times 10^6$ cells were added by micro cover glass and plate was incubated at 37° C. in an atmosphere containing 5% $CO_2$. When 90% of cellular confluence was obtained, cells were washed twice with 2 ml of incomplete DMEM cell culture medium and once with 2 ml of sterile phosphates buffer at pH 7.4. All solutions were quickly added to avoid that cells surface becomes dry. Next, 200 $\mu$l of supernatant H308 hybridoma, containing anti-lipidic particles H308 monoclonal antibody, at 1:10 dilution using incomplete DMEM cell culture medium were added, and cells were incubated for 1 h at 37° C. in presence of 5% $CO_2$. After incubation, cell cultures were washed 3-times with 2 ml of phosphates buffer, pH 7.4 and 200 $\mu$l of FITC-conjugated goat anti-Fc of mouse IgM antibodies at 1:200 dilution, using incomplete DMEM cell culture medium, were added. After incubation for 1 h at 37° C. in presence of 5% $CO_2$ cell cultures were washed 3-times again with 2 ml of phosphates buffer. Finally, micro cover glasses were mounted in slides with VectaShield, these preparations were sealed, observed, and photographed with epifluorescence and optics of Nomarski using a Nikon Optiphot-2 microscope.

Figure 6:
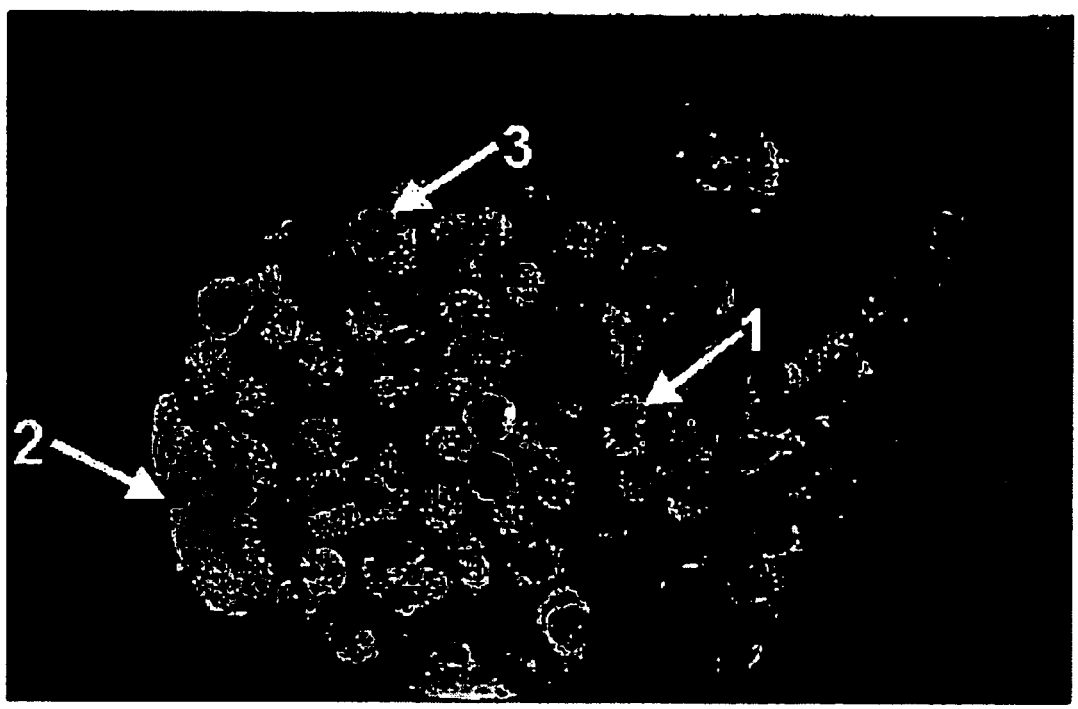
FIG. 6 is a picture of C5337 human pancreas cancer cells that shows the immunoreaction between H308 monoclonal antibody and lipidic particles from the membranes of these cells.

C5337 cancer pancreas cells showed areas with a strong fluorescence intensity located in small points, in occasions above cellular nucleus (1, FIG. 6); in some cases fluorescence was located in cell junctions (2, FIG. 6). In other cases, neoplastic cells were marked in the whole surface, these cells showed a round morphology (3, FIG. 6) as that corresponding to cells that do not adhere to cell culture plates which can be in apoptosis, or programmed cellular death; furthermore, these cells also can not be adhered because they will be in a cellular division process. Immunostaining shows the reaction of monoclonal antibody with lipidic particles present in membranes of C5377 cancer pancreas cells. H308 monoclonal antibody was adsorbed with egg-yolk phosphatidylcholine:phosphatidate liposomes (2:1 molar ratio) in Tris-NaCl buffer (10 mM, 1 mM) pH 7, containing 0.1 $\mu$mol of phosphatidate and treated with $CaCl_2$ 5 mM to induce lipidic particles formation, to confirm that the observed immunostaining was really with cellular lipidic particles. After this adsorption the supernatant of H308 hybridoma no longer showed reaction with C5337 cells because the anti-lipidic particles antibodies from this supernatant were eliminated.

As a negative control, neoplastic cells were incubated with FITC-conjugated second antibody or with an unrelated monoclonal antibody, from IgM isotype, directed against a membranal protein of *Trichinella spiralis*. In both cases there was not any reaction of antibodies with neoplastic cells since fluorescence that showed the immunoreaction was not observed.

These studies show that H308 monoclonal antibody besides reacting with lipidic particles of liposomal membranes, also reacts with membranal lipidic particles from cells in cultures. These cells represent a natural antigen contrary to liposomes that are an experimental model of cellular membranes. When tissue sections (6 μm-thickness) have also been used, as human placenta sections, H308 monoclonal antibody reacted with cellular membranes of this organ. Immunoreaction was different along the 9 months of life of this organ and a higher quantity of lipidic particles was detected in the final stages of pregnancy. This reaction showed that H308 monoclonal antibody also reacts with lipidic particles present in a natural way in this human organ.

In accordance with the above-mentioned studies, detection of lipidic particles in cell membranes can be used to characterize the distinct functional states that cells go through during the different stages of cellular cycle, including the apoptosis process, or programmed cellular death.

Example 3A

Direct Detection by the Cytofluorometry Method of Lipidic Particles in Cells from a Subject Using H308 Monoclonal Antibody A sample of 100,000 plaquettes in 100 ml of Tris-NaCl buffer (10 mM, 135 mM) pH 7, containing glucose 11 mM, was placed in polystyrene 8×75 mm tubes. To each one of these aliquots H308 hybridoma supernatant at 1:100 dilution into Tris-NaCl buffer (10 mM, 135 mM) pH 7, containing glucose 11 mM, was added. This hybridoma generates an anti-lipidic particles monoclonal antibody from de IgM isotype. Additionally, 5 μM adenosin diphosphate (ADP) was added to each one of the tubes and they were incubated for 30 min at 37° C. After incubation, plaquettes were washed with 4 ml of Tris-NaCl buffer (10 mM, 135 mM) pH 7, containing glucose 11 mM. Plaquettes were recovered by centrifugation at 200×g for 5 min. After centrifugation, FITC-conjugated goat anti-Fc of mouse IgM antibodies at 1:200 final dilution, into Tris-NaCl buffer (10 mM, 135 mM) pH 7, containing glucose 11 mM, were added to each tube as second antibody and tubes were incubated for 1 h at 37° C. in the darkness. At the end of the incubation plaquettes were washed as it was indicated previously. Finally, plaquettes were resuspended in 500 μl of FACS Flow solution (Beckton Dickinson Co.) filtered with a 0.22 μm Millipore filter diameter pore.

Plaquettes suspension was analyzed by cytofluorometry in a FACScalibur Flow Cytometer equipped with a single 488 nm laser beam (Beckton Dickinson).

Fluorescence readings were made in the FL-1 channel. Plaquettes relative size and/or plaquettes aggregation were analyzed by diffraction of the laser beam in the FSC channel. Granularity or membranal plaquette complexity was analyzed by refraction and reflection of the laser in the SSC channel. Analysis of 10,000 plaquettes was made with the following detectors: FSC in E00, in a lineal mode with an amplifier gain of 5 V and with a detector compensation threshold of 52 V; SSC of 450 V and FL-1 of 700 V, both in logarithmic mode (Baeza et al., op. cit., 1995). The obtained data were analyzed with the Cellquest program (Beckton Dickinson).

Plaquettes treated as described above but without any ADP activation were used as a negative control of the immunoreaction of them with H308 monoclonal antibody.

Anti-lipidic particles H308 monoclonal antibody showed reactivity with ADP activated plaquettes. Fluorescence histograms of the immunoreaction of plaquettes without any activation or ADP activated were similar to those presented in: a,m, FIG. 4J, Example 2B, for AC31 patient serum and control sera, respectively. Cytofluorometric histograms showed a 10-fold fluorescence increase when ADP activated plaquettes were used as antigens, with D=0.50 at p<0.001. In addition, graphs corresponding to values of membranal activated plaquettes complexity and of activated plaquettes aggregation were as those showed in: n, FIG. 4K; and ñ, FIG. 4L for the indicate sera These results showed the higher complexity in membranal plaquettes during their ADP activation as well as the lack of plaquettes aggregation during this process.

These results show clearly the presence of lipidic particles in plaquettes which are cellular fragments containing a residual membrane which allows to study the structural and functional characteristics of this cellular organelle.

The methodology of this Example can also be used to detect lipidic particles in isolated cells, such as erythrocytes and leukocytes which are in different physiologic states. These studies will allow to characterize the physiologic states of cells by the quantity of lipidic particles that present in their cellular membranes. This knowledge can contribute to maintain cells in a more appropriate functional state and therefore it can contribute to the prevention of illnesses.

Example 3B

Direct Detection by the Cellular-ELISA Method of Lipidic Particles in Cells from a Subject Using Anti-lipidic Particles Antibodies from Sera of Patients with the Antiphospholipid Syndrome C5337 pancreas cancer cells were used as antigens, then $1 \times 10^5$ cells was seeded in each well of a flat-bottom 96-wells microtiter plates, and they were incubated at 37° C. in an atmosphere containing 5% $CO_2$ until cell confluence in the wells reached 100%. After incubation, 200 μl of a blocking solution containing Tris-NaCl buffer (10 mM, 135 mM) pH 7, and 5% fetal calf serum, were added to each one of the wells and microtiter plates were incubated for 30 min at 37° C. Additionally, the blocking solution was eliminated and 100 μl of sera from patients with the antiphospholipids syndrome, or from healthy blood donators at 1:50 final dilution, using blocking solution, were quickly added to avoid that cells surface becomes dry. All solutions were added subsequently in the same way. After cell cultures were incubated for 30 min at 37° C. in an atmosphere containing 5% $CO_2$, they were washed 3-times with 200 μl of blocking solution for 5 min in each washing. Next, 100 μl of peroxidase-conjugated goat anti-Fc of human IgG, IgA and IgM antibodies at 1:2000 dilution, into blocking solution, were added as second antibody. Microtiter plates were incubated for 30 min at 37° C. in an atmosphere containing 5% $CO_2$. After incubation, microtiter plates were washed as it was indicated and 100 µl of peroxidase substrates were added to each one of the wells and plates were again incubated for 20 min at 37° C. Finally 50 µl of 2.5 M sulfuric acid were added to stop the peroxidase reaction and the absorbency was read at 492 nm in an ELISA Labsystems reader Multiskan MS model.

Sera from the thirty patients studied in Examples 1 and 2B presented reaction with the neoplastic cells. Arbitrary units higher than 1 were obtained from the 492 nm absorbance readings. To confirm that this immunoreaction was with lipidic particles present in membranes of C5337 pancreas cancer cells, patients sera were adsorbed with egg-yolk phosphatidylcholine:phosphatidate liposomes (2:1 molar ratio) in Tris-NaCl buffer (10 mM, 1 mM) pH 7, containing 0.1 µmol of phosphatidate, and treated with $CaCl_2$ 5 mM to induce lipidic particles formation. After this adsorption patients sera no longer showed reaction with C5337 pancreas cancer cells because the anti-lipidic particles antibodies were eliminated of them.

Figure 7:
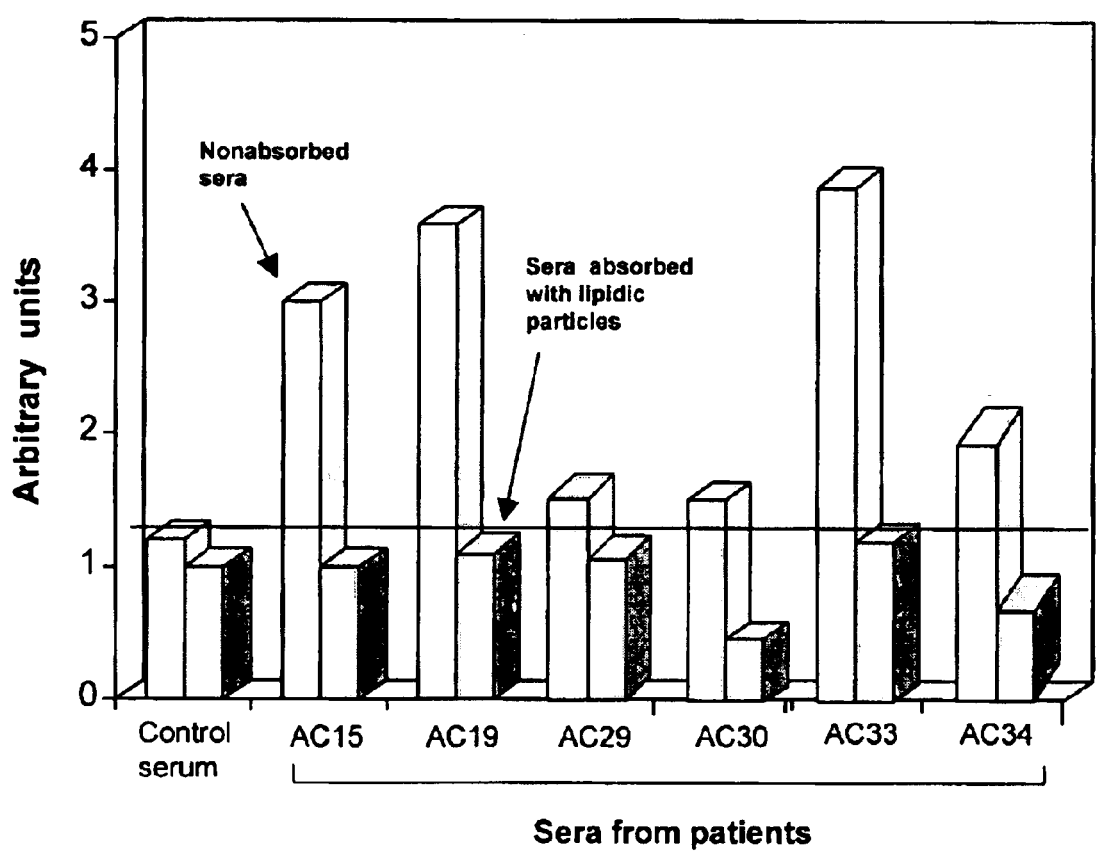
FIG. 7 illustrates the analysis by the cellular-ELISA method of the reaction between sera from patients with the antiphospholipid syndrome and C5337 human pancreas cancer cells; patients sera were used adsorbed and without any adsorption with liposomal antigens made from PC:PA (2:1 mole ratio) bearing lipidic particles induced by calcium.

Results obtained with some patients sera are showed in FIG. 7. These sera are: AC15, AC30 and AC33 from patients with primary antiphospholipid syndrome; AC19 and AC29 from patients with systemic lupus erythematosus, and AC34 from a patient with antiphospholipid syndrome secondary to systemic lupus erythematosus. Bar graphs to of the direct reaction of patients sera with C5337 cells as well as of the reaction of patients sera after their adsorption with liposomes bearing lipidic particles are showed in FIG. 7. It can be seen that the reaction of sera with cellular antigens was eliminated after their adsorption with liposomes bearing lipidic particles because the anti-lipidic particles antibodies that they contained were eliminated. C5337 cells were incubated with a serum from a healthy blood donator (FIG. 7) as a negative control of the reaction of human sera with cellular lipidic particles. In FIG. 7 the dark line indicates the uper limit above of which the reactions of sera with cellular antigens are positive.

These experiments are very important because they show that the anti-lipidic particles antibodies of sera from ill subjects, which were primary detected with experimental membrane models such as liposomes, also showed reaction with the lipidic particles of cellular antigens, which really represent a natural antigen as those found in humans and animals.

Example 3C

Direct Detection by the Immunofluorescence Method of Lipidic Particles in Cells from a Subject Using Anti-lipidic Particles Antibodies from Sera of Patients with the Antiphospholipid Syndrome This detection was carried out as it was indicated in the Example 3, with the difference that C5337 pancreas cancer cells were incubated with sera from patients with the antiphospholipid syndrome bearing anti-lipidic particles antibodies instead of H308 monoclonal antibody. Patients' sera were used at 1:50 dilution and FITC-conjugated goat anti-Fc of human IgG, IgA and IgM antibodies were used as second antibody.

Neoplastic cell cultures were marked with the anti-lipidic particles antibodies from patients' sera in a similar way as it was described for C5337 pancreas cancer cells in FIG. 6, from Example 3, showing the binding of lipidic particles from neoplastic membranes with these anti-lipidic particles antibodies.

On the other hand, the methodology described in this Example can be applied in an alternative way to the detection of anti-lipidic particles antibodies in patients' sera when these antibodies have been not yet detected by the procedures indicated in the Examples 1 and 2B.

From previous examples, we can conclude that in another favorite modality of the present invention, a diagnosis kit particularly useful for the direct detection of lipidic particles in cellular antigens includes: at least an indicator reagent including at least an anti-lipidic particles monoclonal antibody; at least a buffer solution as a medium to allow the reaction to proceed; and fluorescent or enzymatic procedures to make evident this reaction.

In this preferred embodiment of the diagnosis kit, the cell samples coming from the ill individual are made react with anti-lipidic particles monoclonal antibody, in other words, with the indicator reagent.

In an alternative embodiment of the diagnosis kit, instead of the anti-lipidic particles monoclonal antibody, it can be used at least a patient serum in which anti-lipidic particles antibodies have been previously demonstrated by using the methodology described in Examples 1 and 2B.

In an alternative embodiment, the diagnosis kit includes as some part of it one or more microtiter plate(s) for cellular culture, or centrifuge tube(s) as recipient(s) for the development of the reaction.

In another preferred embodiment of the present invention, a kit for the detection of lipidic particles in cells in different physiologic states coming from a human or animal subject, includes: at least an indicator reagent including at least an anti-lipidic particles monoclonal antibody; at least a buffer solution as a medium to allow the reaction; and fluorescent or enzymatic procedures to make evident this reaction.

In this preferred embodiment of the detection kit, cell samples in different physiologic states are made react with the anti-lipidic particles monoclonal antibody, in other words, with the indicator reagent.

In an alternative embodiment, the kit of detection of lipidic particles in cells in different physiologic states includes as some part of it one or more microtiter plate(s) for cellular culture, or centrifuge tube(s) as recipient(s) for the development of the reaction.

Example 4

Obtention of Mice that Produce Anti-lipidic Particles Antibodies by Immunization with Liposomes Bearing Lipidic Particles Induced by Manganese Ten, 2-months age, BALB/c female mice were immunized by intrasplenic injection of 100 µg of egg-yolk phosphatidylcholine:phosphatidate liposomes (2:1 molar ratio) in Tris-NaCl buffer (10 mM, 1 mM) pH 7, containing 0.1 µmol of phosphatidate, and treated with $MnCl_2$ 5 mM to induce lipidic particles formation. Intrasplenic immunization was repeated 2-weeks later by the method described by Nilsson et al. (op. cit. 1987). Additionally, BALB/c female mice were intraperitoneally injected with the same liposomes dose 2-weeks later, then they were boosted 4-times at 2-weeks intervals.

After seven days of the last immunization female mice were bled from the orbital sinus to analyze the presence of anti-lipidic particles antibodies in the obtained sera. Using this immunization procedure, 60% of the immunized BALB/c female mice produced anti-lipidic particles antibodies.

Immunoreaction analysis of mice sera was made by the liposomal cytofluorometry method. Egg-yolk phosphatidylcholine:phosphatidate liposomes (2:1 molar ratio) in Tris-NaCl buffer (10 mM, 1 mM) pH 7, containing 0.1 μmol of phosphatidate, and treated with 5 mM $MnCl_2$ to induce lipidic particles formation were used as antigens. Analysis of 10,000 liposomas was made in logarithmic mode with the following detectors: FSC in E00, with a detector compensation threshold of 52V; SSC of 401 V and FL-1 of 748 V (Baeza et al., op. cit., 1995). The obtained data were analyzed with the Cellquest program (Beckton Dickinson).

Figure 8:
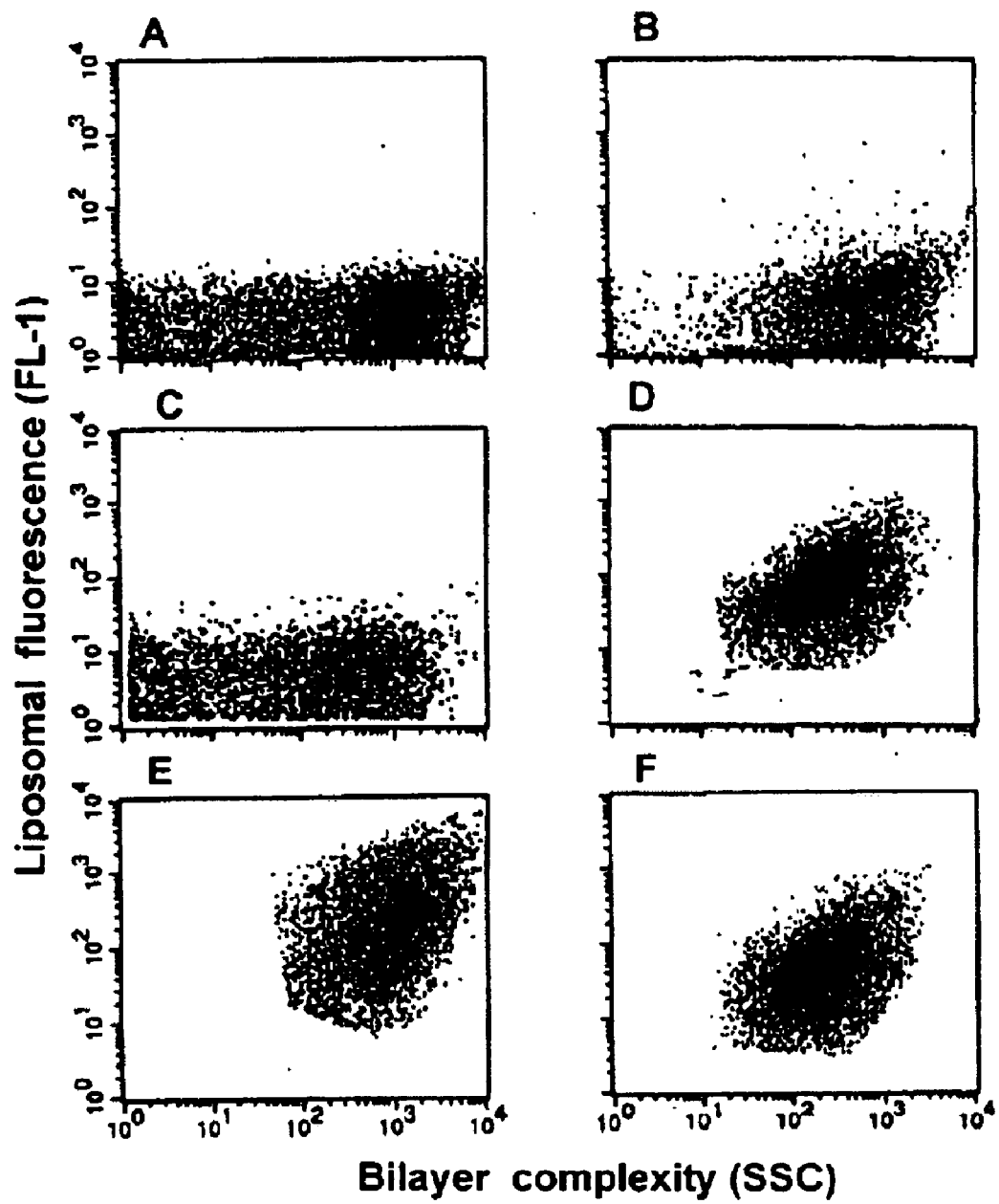
FIGS. 8A–8F show the graphs of liposomal fluorescence and liposomal bilayers complexity which analyze the reaction between liposomal antigens and sera from BALB/c mice before or after they were immunized with PC:PA (2:1 mole ratio) liposomes bearing lipidic particles induced by manganese. Liposomal antigens used in immunoreactions were the same ones used for mice immunization.

Autofluorescence and lipidic bilayer complexity (SSC) of liposomes treated with $MnCl_2$ (FIG. 8A) were not modify when these liposomes were also incubated with FITC-conjugated goat anti-Fc of mice IgG, IgA and IgM antibodies as second antibody (FIG. 8B). Because in absence of anti-lipidic particles antibodies the second antibody do not bind directly to liposomes.

Mice sera were incubated with liposomal antigens and to detect the immunoreaction they were used FITC-conjugated goat anti-Fc of mice IgG, IgA and IgM antibodies as second antibody. Sera analyzed were obtained before mice were immunized as well as after the immunization with liposomal antigens.

Sera from mice before they were immunized did not show any reaction with lipidic particles, since fluorescence and values of their lipidic bilayer complexity (SSC) were similar to those of control liposomes that were treated only with manganese (FIG. 8A). Sera were mixed and they were used as a negative control of mice sera immunoreaction with lipidic particles (FIG. 8C).

Sera from mice after they were immunized with liposomal antigens treated with manganese showed an immunoreaction that produce a liposomal fluorescence 10 to 100-fold higher than the reaction of mice control sera (FIG. 8C), with values of $D \geq 0.5$ at $p<0.001$. As example, cytofluorometry graphs of the reaction of serum from RB11, RB14 and RB17 mice are showed in FIGS. 8D, 8E and 8F. Reaction between the antibodies of sera from these mice and lipidic particles although positive, was different for each serum, with values of D=0.9, D=0.91 and D=0.79, respectively, which can be attributed to the polyclonal origin of these antibodies. SSC values from immunoreaction (FIGS. 8D, 8E and 8F) were similar to those of liposomes control incubated with manganese (FIG. 8A), and they showed the presence of lipidic particles which give the reaction with the anti-lipidic particles antibodies from mice sera.

Figure 9:
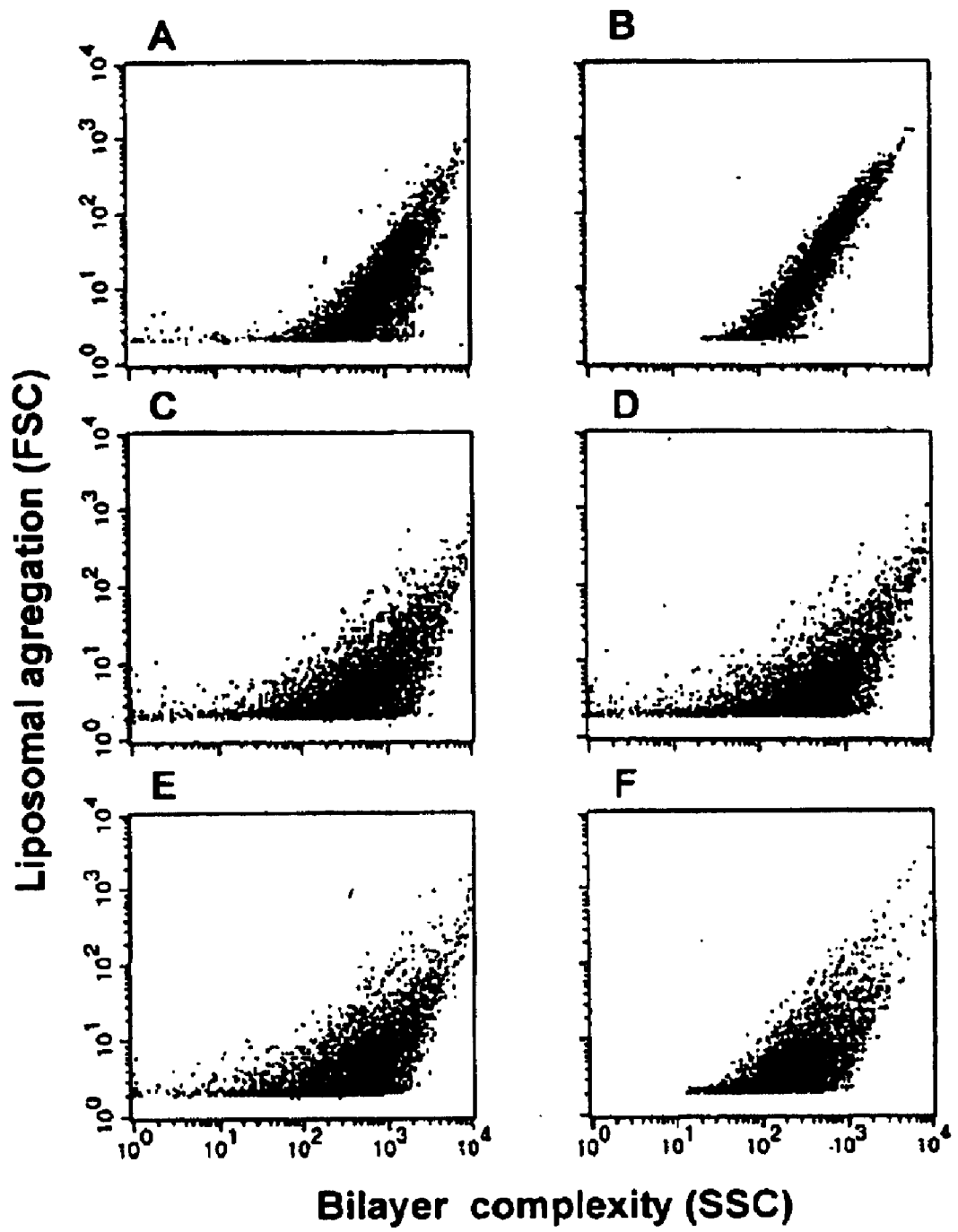
FIGS. 9A–9F show the graphs of liposomal aggregation and liposomal bilayers complexity which analyze the reaction between liposomal antigens and sera from BALB/c mice before or after they were immunized with PC:PA (2:1 mole ratio) liposomes bearing lipidic particles induced by manganese. Liposomal antigens used in immunoreactions were the same ones used for mice immunization.

Furthermore, the reaction of immunized mice sera with lipidic particles did not show any liposomal aggregation, that could increase in unspecific way the fluorescence registered and to give a positive false result, since FSC values after the immunoreaction (FIGS. 9D–9F) were similar to those of liposomes incubated with manganese (FIG. 9A), or with the second antibody (FIG. 9B), or with mice sera before the immunization (FIG. 9C). SSC values in FIGS. 9A–9F also showed the presence of lipidic particles in liposomal antigens as it was described in FIGS. 8A–8F.

In mice immunized with liposomes bearing lipidic particles induced by manganese, after the detection of anti-lipidic particles antibodies they were also detected anti-cardiolipin antibodies, anti-nuclear and anticoagulant antibodies. These findings confirm our hypothesis which propose that anti-lipidic particles antibodies constitute the first stage in the development of illnesses associated with antiphospholipid antibodies. The mouse that gave the highest reaction with lipidic particles, was the RB14 with a value of D=0.91, and it was used in the obtention of anti-lipidic particles monoclonal antibodies.

Example 4A

Obtention of Mice that Produce Anti-lipidic Particles Antibodies by Immunization with Liposomes Bearing Lipidic Particles Induced by Chlorpromazine or Procainamide Ten, 2-months age, BALB/c female mice were immunized by intrasplenic injection of 100 μg of egg-yolk phosphatidylcholine:phosphatidate liposomes (2:1 molar ratio) in Tris-NaCl buffer (10 mM, 1 mM) pH 7, containing 0.1 μmol of phosphatidate, and treated with the lipidic particles inducer drug procainamide at a concentration of 8 mM. Immunization was carried out as it was indicated in Example 4. After seven days of the last immunization female mice were bled from the orbital sinus to analyze the presence of anti-lipidic particles antibodies in the obtained sera. Using this immunization procedure, 70% of the immunized BALB/c female mice produced anti-lipidic particles antibodies.

Immunoreaction analysis of mice sera was made by the liposomal cytofluorometry method as it was indicated in Example 4. Egg-yolk phosphatidylcholine:phosphatidate liposomes (2:1 molar ratio) in Tris-NaCl buffer (10 mM, 1 mM) pH 7, containing 0.1 μmol of phosphatidate, and treated with 8 mM procainamide to induce lipidic particles formation were used as antigens. Analysis of 10,000 liposomas was made in logarithmic mode as it was described in Example 4.

Figure 10:
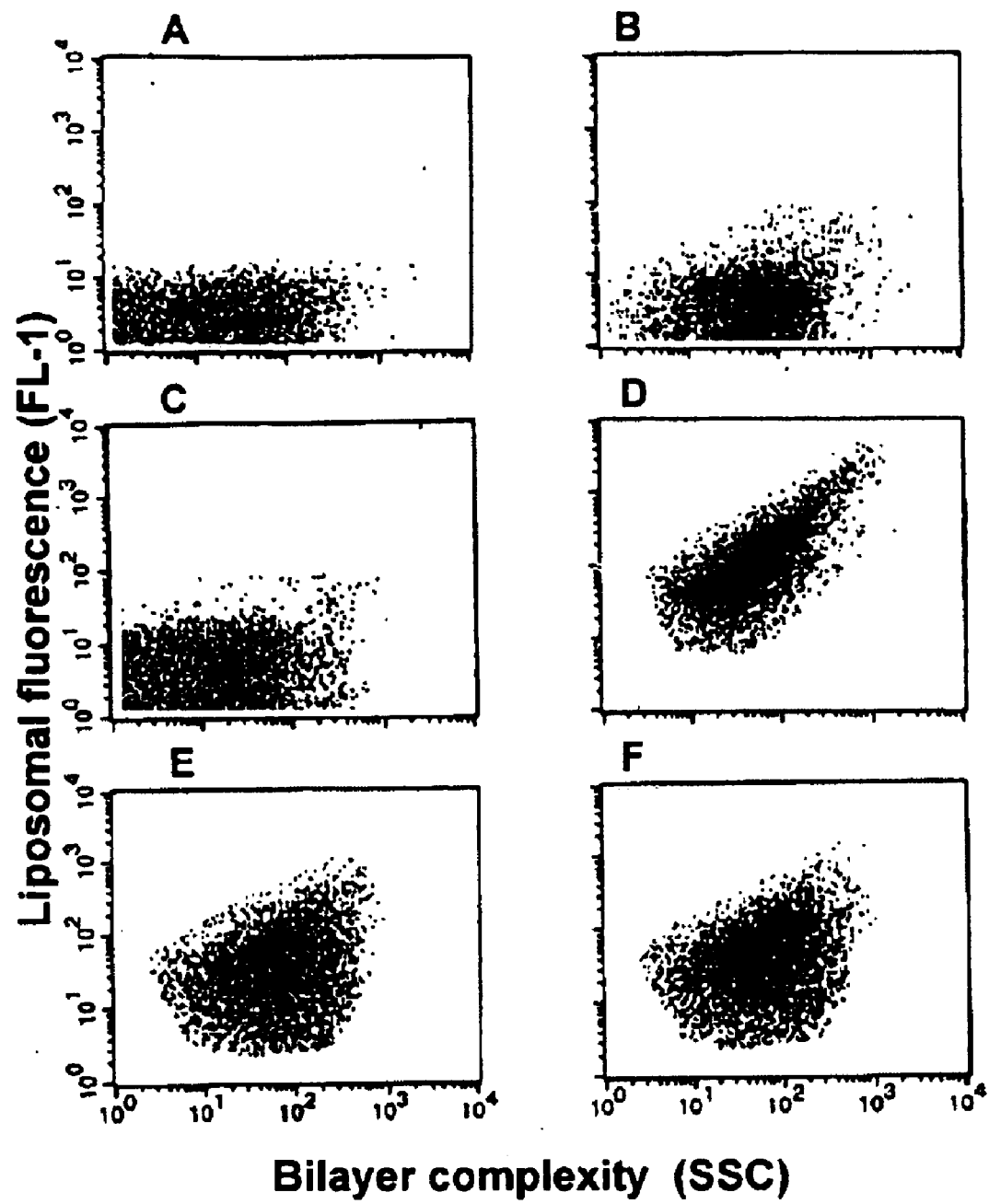
FIGS. 10A–10F show the graphs of liposomal fluorescence and liposomal bilayers complexity which analyze the reaction between liposomal antigens and sera from BALB/c mice before or after they were immunized with PC:PA (2:1 mole ratio) liposomes bearing lipidic particles induced by procainamide. Liposomal antigens used in immunoreactions were the same ones used for mice immunization.

Autofluorescence and lipidic bilayer complexity (SSC) of liposomes treated with procainamide (FIG. 10A) were not modify when these liposomes were also incubated with FITC-conjugated goat anti-Fc of mice IgG, IgA and IgM antibodies as second antibody (FIG. 10B). Because in absence of anti-lipidic particles antibodies the second antibody do not bind directly to liposomes bearing lipidic particles induced by procainamide.

Mice sera were incubated with liposomal antigens and to detect the immunoreaction they were used FITC-conjugated goat anti-Fc of mice IgG, IgA and IgM antibodies as second antibody. Sera analyzed were obtained before mice were immunized as well as after the immunization with liposomal antigens bearing lipidic particles induced by procainamide.

Sera obtained before mice were immunized did not show any reaction with lipidic particles, since fluorescence and values of their lipidic bilayer complexity (SSC) were similar to those of control liposomes that were treated only with procainamide (FIG. 10A). Sera obtained before mice immunization were mixed and the mixture was used as a negative control of mice sera immunoreaction with lipidic particles (FIG. 10C).

Sera obtained after mice were immunized with liposomal antigens treated with the lipidic particles inducer drug procainamide showed an immunoreaction that produce a liposomal fluorescence 10 to 100-fold higher than the reaction of control mice sera (FIG. 10C), with values of $D \geq 0.5$ at $p<0.001$. As example, cytofluorometry graphs of the reaction of serum from RF11, RF14 and RF17 mice are showed in FIGS. 10D, 10E and 10F, respectively. Reaction between the antibodies of sera from these mice and lipidic particles although positive, was different for each serum, with values of D=0.8, D=0.72 and D=0.67, respectively, which can be attributed to the polyclonal origin of these antibodies. SSC values from immunoreaction (FIGS. 10D, 10E and 10F) were similar to those of liposomes control incubated with procainamide (FIG. 10A), and they showed the presence of lipidic particles in liposomes which give the reaction with the anti-lipidic particles antibodies from mice sera.

Furthermore, the reaction of sera from immunized mice did not produce any liposomal aggregation, that could increase in unspecific way the fluorescence registered and to give a positive false result, since FSC values after the immunoreaction were similar to those of liposomes incubated with procainamide, or with the second antibody, or with mice sera before the immunization in a similar way as it was described in FIGS. 9A–9F.

Similar results to those shown in FIGS. 10A–10F were obtained when mice were immunized with liposomes bearing lipidic particles induced by the lipidic particles inductor drug chlorpromazine at a concentration of 3 mM.

Figure 11:
FIG. 11 is a photograph of a seven (7) month old BALB/c female mouse immunized with PC:PA (2:1 mole ratio) liposomes bearing lipidic particles induced by chlorpromazine, where alopecia and lesions on the face in the form of butterfly wings are observed.

After the detection of anti-lipidic particles antibodies in immunized mice anti-cardiolipin antibodies, anti-nuclear and anticoagulant antibodies were also detected in them, in a similar fashion as it was described for mice immunized with liposomes treated with manganese, from Example 4. These findings corroborate that anti-lipidic particles antibodies constitute the first stage in the development of illnesses associated with antiphospholipid antibodies. Furthermore, in mice immunized with liposomes incubated with procainamide or chlorpromazine it has been demonstrated the presence of deposits of immune complexes in different organs. In addition, these mice developed alopecia and lesions in the face in the form of butterfly wings similar to those that have been described in human systemic lupus erythematosus. In FIG. 11 the picture of a 7-months age BALB/c female mouse that was treated with liposomes bearing lipidic particles induced by chlorpromazine, where alopecia and lesions in the face in the form of butterfly wings can be observed.

This animal model indicates that antigens bearing lipidic particles induced by chlorpromazine or procainamide were more efficient in developed in BALB/c female mice not only anti-lipidic particles antibodies, but a pathology that is more similar to the one that is presented in humans.

Example 4B

Obtention of Mice that Produce Anti-lipidic Particles Antibodies by Immunization with the Drugs Chlorpromazine or Procainamide For this treatment the immunization procedure indicated in Example 4A was modified since chlorpromazine or procainamide drugs were administered directly in absence of liposomal antigens to BALB/c female mice.

Ten, 2-months age, BALB/c female mice were immunized by intramuscular injection of the lipidic particles inducer drugs chlorpromazine or procainamide, using 3 mg/Kg, of body weight, for chlorpromazine and 10 mg/Kg, of body weight, for procainamide, each 24 hs, for 2-months. Drug doses were similar to those that are administered in the medical treatment of humans; in psychotic and maniacs dysfunctions for chlorpromazine and those that were used for the treatment of cardiac arrhythmias for procainamide.

After seven days of the last intramuscular injection female mice were bled from the orbital sinus to analyze the presence of anti-lipidic particles antibodies in the obtained sera. Using this immunization procedure, 50% of the immunized BALB/c female mice produced anti-lipidic particles antibodies.

Immunoreaction analysis of mice sera was made by the liposomal cytofluorometry method as it was indicated in Example 4. Egg-yolk phosphatidylcholine:phosphatidate liposomes (2:1 molar ratio) in Tris-NaCl buffer (10 mM, 1 mM) pH 7, containing 0.1 µmol of phosphatidate, and treated with 8 mM procainamide to induce lipidic particles formation were used as antigens. Analysis of 10,000 liposomas was made in logarithmic mode as it was described in Example 4.

Mice sera were incubated with liposomal antigens and to detect the immunoreaction they were used FITC-conjugated goat anti-Fc of mice IgG, IgA and IgM antibodies as second antibody. Sera analyzed were obtained before mice were treated with the lipidic particles inducer drugs as well as after of these treatments.

Figure 12:
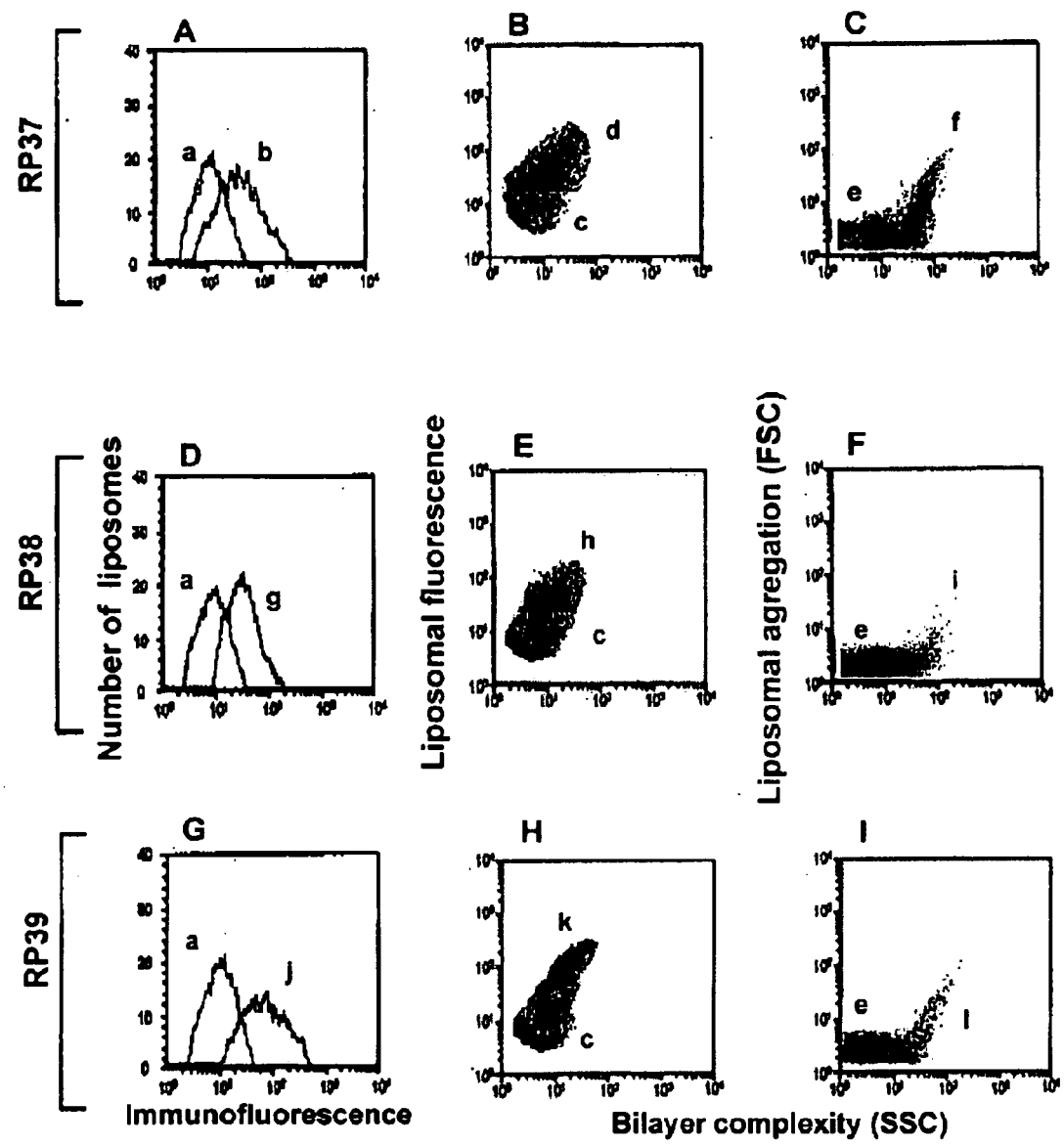
FIGS. 12A–12I are the cytofluorometric analysis of the reaction between liposomal antigens and sera from BALB/c mice before or after they were treated by intramuscular injection each 24 hs during 2-months with 3 mg/Kg, of body weight, of the lipidic particles inducer drug procainamide. Liposomal antigens used in immunoreactions were made from PC:PA (2:1 mole ratio) bearing lipidic particles induced by procainamide.

Sera obtained from mice after they were treated with the lipidic particles inducer drug procainamide showed an immunoreaction that produce a liposomal fluorescence 4-fold higher than the reaction of mice sera before treatment (a, FIGS. 12A, D, and G), with values of D≧0.5 at p<0.001. As example, cytofluorometry graphs of the reaction of serum from RP37, RP38 and RP39 mice are showed in: b, FIG. 12A; g, FIG. 12D; and j, FIG. 12G. Reaction between the antibodies of sera from these mice and lipidic particles although positive, was different to each serum, with values of D=0.58, D=0.68 and D=0.8, respectively, which can be attributed to the polyclonal origin of these antibodies. SSC values from immunoreaction showed in: d, FIG. 12B; h, FIG. 12E; and k, FIG. 12H were similar to those of liposomes control incubated with procainamide (FIG. 10A), and they showed the presence of lipidic particles which give the reaction with the anti-lipidic particles antibodies from mice sera.

Furthermore, the reaction of immunized mice sera with lipidic particles did not show any liposomal aggregation, since FSC values after the immunoreaction (f, FIG. 12C; i, FIG. 12F; and l, FIG. 12I) were similar to those of liposomes incubated with manganese (FIG. 9, Example 4), or with mice sera before mice were treated with the lipidic particles inducer drug procainamide (e, FIGS. 12C, F and I).

Anti-lipidic particles antibodies were also detected before than anti-cardiolipin antibodies, anti-nuclear and anticoagulant antibodies in these mice, in a similar way as it was described for mice in Examples 4 and 4A. Furthermore, the presence of deposits of immune in different organs and the development of alopecia and lesions in the face in the form of butterfly wings were also showed in these mice.

These results indicate that the lipidic particles inducer drugs chlorpromazine or procainamide induce the formation of lipidic particles in the membranes of mice cells which subsequently induce the production of anti-lipidic particles antibodies and the development of a pathology similar to the human antiphospholipid syndrome secondary to systemic lupus erythematosus. The formation of lipidic particles by the lipidic particles inducer drugs chlorpromazine or procainamide in liposomes has been previously demonstrated by nuclear magnetic resonance (Baeza et al., op. cit., 1995; Aguilar, op. cit., 1997; Aguilar et al., op. cit., 1999).

Example 4C

Obtention of Producing Anti-lipidic Particles Antibodies Mice by Passive Immunization with the Anti-lipidic Particles H308 Monoclonal Antibody For this treatment the immunization procedure indicated in Example 4 was modified since passive immunization of BALB/c female mice was carried out.

Ten, 2-months age, BALB/c female mice were immunized by intraperitoneal injection of 1 µg of anti-lipidic particles H308 monoclonal antibody, each week, for 2-months. After seven days of the last intraperitoneal injection female mice were bled from the orbital sinus to analyze the presence of anti-lipidic particles antibodies in the obtained sera. Using this immunization procedure, 80% of the immunized BALB/c female mice produced anti-lipidic particles antibodies.

Immunoreaction analysis of mice sera was made by the liposomal cytofluorometry method as it was indicated in Example 4. Egg-yolk phosphatidylcholine:phosphatidate liposomes (2:1 molar ratio) in Tris-NaCl buffer (10 mM, 1 mM) pH 7, containing 0.1 μmol of phosphatidate, and treated with 5 mM $CaCl_2$ to induce lipidic particles formation were used as antigens. Analysis of 10,000 liposomas was made in logarithmic mode as it was described in Example 4.

Mice sera were incubated with liposomal antigens and to detect the immunoreaction they were used FITC-conjugated goat anti-Fc of mice IgG, IgA and IgM antibodies as second antibody. Sera analyzed were obtained before mice were treated by passive immunization with the anti-lipidic particles H308 monoclonal antibody as well as after mice received this immunization procedure.

Sera obtained after mice were treated by passive immunization with the anti-lipidic particles H308 monoclonal antibody showed the presence of anti-lipidic particles antibodies in them; since cytofluorometry graphs of the reaction of passive immune mice sera with liposomes bearing lipidic particles induced by $CaCl_2$ were similar to those described in FIGS. 8, 9, 10 and 12 which showed anti-lipidic particles antibodies induced by different antigens containing lipidic particles.

Anti-lipidic particles antibodies were also detected before than anti-cardiolipin antibodies, anti-nuclear and anticoagulant antibodies in these mice, in a similar way as it was described for mice in Examples 4, 4A, and 4B. Additionally, the presence of deposits of immune complexes in different organs and the development of alopecia and lesions in the face in the form of butterfly wings were also showed in these mice.

These results showed the direct participation of anti-lipidic particles antibodies in the development in BALB/c female mice of a pathology similar to the human antiphospholipid syndrome secondary to systemic lupus erythematosus. Therefore, a possible treatment of these illnesses would be by the inhibition of anti-lipidic particles antibodies and/or by the stabilization of cellular membranes that prevent the formation of lipidic particles, as it is subsequently described.

Example 5

Obtention of Hybridomas by Fusion of P3X63Ag8U.1 Cells with Spleen Cells of a Producing Anti-lipidic Particles Antibodies BALB/c Female Mouse Four days before the planned fusion, three mice previously immunized by intrasplenic and intraperitoneal injection of 100 μl of egg-yolk phosphatidylcholine:phosphatidate liposomes (2:1 molar ratio) in Tris-NaCl buffer (10 mM, 1 mM) pH 7, containing 0.1 μmol of phosphatidate, and treated with 5 mM MnCl2 to induce lipidic particles formation, were boosted by intravenous tail vein injection using the same liposomes dose. The rational way is to initiate secondary immune responses selectively in the spleen as opposed to lymph nodes. Therefore the mouse producing the higher titer of anti-lipidic particles antibodies were chosen for hybridoma production.

The spleen of the RB14 BALB/c female mouse producing the higher titers of anti-lipidic particles antibodies was removed under sterility conditions and it was placed in a petri dish with 6 ml of incomplete DMEM cell culture medium. Spleen mouse was dispersed until a suspension of single cells was obtaining using blunt tips pincers. Cellular suspension was transferred to a 15-ml falcon tube and it was left in repose so that the thick residuals settle down. Next, cellular suspension was transferred to another falcon tube and it was centrifuged at 17×g for 7 min. Subsequently the supernatant was decanted and cellular pellet was resuspended by gently agitation and cellular suspension was diluted by the addition, drop by drop, of 10 ml of incomplete DMEM cell culture medium. Cellular suspension was centrifuged as it was already indicated, then the supernatant was decanted and 4 ml of 0.16 M $NH_4Cl$ were added for erythrocytes lysis. In this step the tube containing cellular suspension was incubated at 37° C. and it was gently rotated during 4 min. Later on 6 ml of incomplete DMEM cell culture medium was added and cellular suspension was centrifuged at 17×g for 7 min. After centrifugation the supernatant was decanted and cellular pellet was gently resuspended in 10 ml of incomplete DMEM cell culture and was allowed to stand at room temperature until their were used (Köhler and Milstein, 1975. Nature 256:495.497).

On the other hand, P3x63Ag8U.1 myeloma cells were collected from cell culture plates and transferred to falcon tubes. Aliquots from P3x63Ag8U.1 myeloma cells and mouse spleen cells were treated with trypan blue and they were counted in a Neubauer camera. The viability of both cellular suspension were higher than 95%. P3x63Ag8U.1 myeloma cells and mouse spleen cells were mixed in a 1:1 cellular proportion, using 36×10$^6$ cells of each cellular type, later cellular mixture was washed with 10 ml of incomplete DMEM cell culture medium. After centrifugation at 17×g for 5 min the supernatant was decanted and cellular pellet was gently resuspended. Subsequently, 1 ml of 4000 polyethyleneglycol solution was added drop by drop, during 1 min, and the mixture was manually shaken up for 1.5 min, then 1 ml of incomplete DMEM cell culture medium was added for 30 sec with slow tube rotation. Next, 3 ml of incomplete DMEM cell culture medium was added for 30 sec also with slow tube rotation, later 16 ml of the same medium was added for 1.5 min with gently agitation. Finally the volume of the fused cell suspension was completed to 40 ml with incomplete DMEM cell culture medium and fused cell suspension was incubated without agitation for 5 min at room temperature. Later on fused cell suspension was centrifuged at 17×g for 5 min, the supernatant was decanted and fused cell pellet was washed again with 40 ml of incomplete DMEM medium. Fused cell pellet was resuspended in 30 ml of selection DMEM-HAT medium and aliquots of 100 μl of this fused cell suspension were seeded in each one of the wells of three 96-wells flat-bottom microtiter plates which 24 hs before cell fusion were seeded with macrophages as feeder cells. Microtiter plates were incubated at 37° C., in an atmosphere with 5% of $CO_2$. After five or eight days of the cellular fusion hybridomas were fed with 50 μl of selection DMEM-HAT medium, finally after 11 days of the cellular fusion hybridoma supernatants were changed by 100 μl of DMEM-HAT media.

After hybridomas growing the supernatants were screened by the liposomal-ELISA method in order to detect the production of anti-lipidic particles antibodies by them. Cellular samples from all hybridomas producing anti-lipidic particles monoclonal antibodies were frozen at −70° C. in liquid nitrogen. Later, 10 hybridomas with high anti-lipidic particles monoclonal antibodies titers were chosen (Table 3) and they were cloned again by limiting dilutionin 96-wells flat-bottom microtiter plates. After hybridomas growing supernatants were screened again by the liposomal-ELISA method and those producing the higher titers of anti-lipidic particles monoclonal antibodies were cultivated in 250 ml bottles for the massive obtention of supernatants containing these antibodies.

TABLE 3

Hybridomas producing anti-lipidic particles antibodies.

| Hybridoma | Arbitrary Units | Hybridoma | Arbitrary Units |
|---|---|---|---|
| H40 | 26 | H120 | 36 |
| H65 | 32 | H121 | 35 |
| H70 | 3 | H176 | 42 |
| H90 | 22 | H200 | 30 |
| H110 | 23 | H308 | 48 |

Example 6

Detection of the Inhibition of Anti-lipidic Particles H308 Monoclonal Antibody Using Phosphorylated Haptens by the Liposomal-ELISA Method Costar microtiter plates, with 96 flat-bottom wells with a high lipidic antigens binding property (Costar Co. Cambrige, USA) were coated by the addition to each one of the wells of 100 $\mu$l of liposomes made from egg-yolk phosphatidylcholine:phosphatidate (2:1 molar ratio) in Tris-NaCl buffer (10 mM, 1 mM) pH 7, containing 0.1 $\mu$mol of phosphatidate, and treated with 5 mM $CaCl_2$ to induce lipidic particles formation. Microtiter plates were incubated at room temperature for 1 h and they were blocked for 1 h at room temperature in a similar way as was described in Example 1. Next, blocking solution was discarded by suction and 100 $\mu$l of H308 monoclonal antibody that was previously incubated with the phosphorylated haptens were added immediately to each one of the wells, to avoid that they becomes dry off.

Phosphorylcholine, glycerolphosphorylcholine, phosphorylserine, glycerol-phosphorylserine and phosphorylethanolamine were used as haptens in quantities of 0.2, 0.4, 0.6, 0.8 and 1.0 $\mu$mol. The chemical structure of these haptens is presented in FIG. 13. Phosphorylcholine and glycerolphosphorylcholine constitute part of the polar region of the lipid phosphatidylcholine, as well as phosphorylserine and glycerolphosphorylserine constitute part of the polar region of phosphatidylserine, and phosphorylethanolamine is part of phosphatidylethanolamine.

Aliquots of 100 $\mu$l of H308 monoclonal antibody were incubated with 100 $\mu$l of each one of the hapten solutions for 30 min at 30° C. Later on, the liposomal-ELISA method was applied as it was described in Example 1. Peroxidase-conjugated goat anti-Fc of mouse IgM antibodies were used as second antibody.

When phosphorylcholine was used as hapten to blocking H308 monoclonal antibody a decrease in the immunoreaction of this antibody with liposomal antigens bearing lipidic particles was observed. This decrease gave an absorbance at 492 nm of 0.06, with 0.6 $\mu$moles of hapten (E, FIG. 14) which represent a 82% inhibition in immunoreaction with regard to reaction in absence of hapten (A, FIG. 14). With 0.2 $\mu$moles of glycerol-phosphorylcholine an 100% inhibition of H308 monoclonal antibody was showed (F, FIG. 14). On the other hand, glycerolphosphorylserine (B, FIG. 14), phosphorylserine (C, FIG. 14) and phosphorylethanolamine (D, FIG. 14) do not cause any inhibition of H308 monoclonal antibody reaction with lipidic particles in liposomes.

Figure 13:
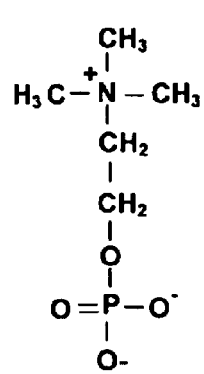
FIG. 13 illustrates outlines of the chemical structure of phosphorylcholine, glycerolphosphorylcholine, phosphorylserine, glycerolphosphorylserine and phosphoryl-ethanolamine that are used as haptens in the inhibition of anti-lipidic particles antibodies.
Figure 13:
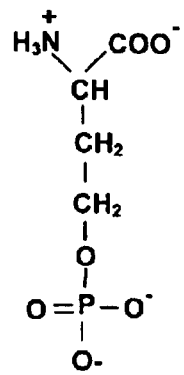
Figure 13:
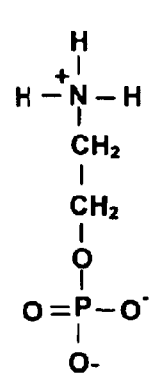
Figure 13:
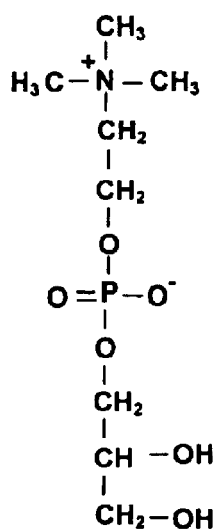
Figure 13:
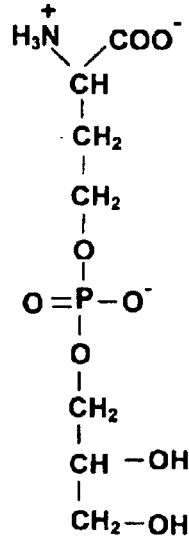

Inhibition of H308 monoclonal antibody reaction with phosphorylcholine and glycerolphosphorylcholine indicate that the antigen recognition domain in H308 monoclonal antibody has subdomains that recognize specifically the choline methyl groups which lacks ethanolamine and serine (FIG. 13). In addition, total immunoreaction inhibition attained by glycerolphosphorylcholine suggests that the antigen domain that recognize H308 monoclonal antibody include chemical groups of glycerol. These findings are in agreement with the structural pattern proposed for the lipidic particle (Cullis et al., op. cit., 1991) (FIG. 15) where monolayer lipids (C, FIG. 15) that recover the molecular arrangement different to bilayer (B, FIG. 15) are more separate than lipids that constitute a normal monolayer (A, FIG. 15). In an open monolayer (C, FIG. 15) glycerolphosphorylcholine is more exposed than in a normal bilayer therefore this is the region in which the H308 monoclonal antibody reacts.

Possibly the central domain of lipidic particle, the region that is observed as inverted micella in: B, FIG. 15, is formed by conic shaped lipids such as phosphatidate. In contrast, monolayers most open than a normal monolayer would be formed by phosphatidylcholine and they would be the regions that identify the H308 monoclonal antibody. If H308 monoclonal antibody reacts specifically with a phosphatidylcholine open monolayer, is clear that this antibody does not show any immunoreaction with liposomes formed exclusively by phosphatidylcholine (G, FIG. 14), because in these liposomes the lipids are in a normal monolayer association that constitute the bilayer, in consequence no immunoreaction with H308 monoclonal antibody is detected.

Example 6A

Detection by the Liposomal-ELISA Method of Glycerolphosphorylcholine Hapten Inhibition of Anti-lipidic Particles Antibodies from Sera of Patients with the Antiphospholipid Syndrome Costar microtiter plates, with 96 flat-bottom wells with a high lipidic antigens binding property (Costar Co. Cambrige, USA) were coated by the addition to each one of the wells of 100 $\mu$l of liposomes made from egg-yolk phosphatidylcholine:phosphatidate (2:1 molar ratio) in Tris-NaCl buffer (10 mM, 1 mM) pH 7, containing 0.1 $\mu$mol of phosphatidate, and treated with 5 mM $CaCl_2$ to induce lipidic particles formation.

Aliquots of 100 $\mu$l of patients' sera that were analyzed in Examples 1 and 2B were incubated with 100 $\mu$l of 0.2 $\mu$moles of glycerolphosphorylcholine for 30 min at 30° C. Later on, blocked patients sera were added to the wells of the microtiter plate and the liposomal-ELISA method was applied as it was described in Example 1. Peroxidase-conjugated goat anti-Fc of human IgG, IgA and IgM antibodies were used as second antibody.

Figure 14:
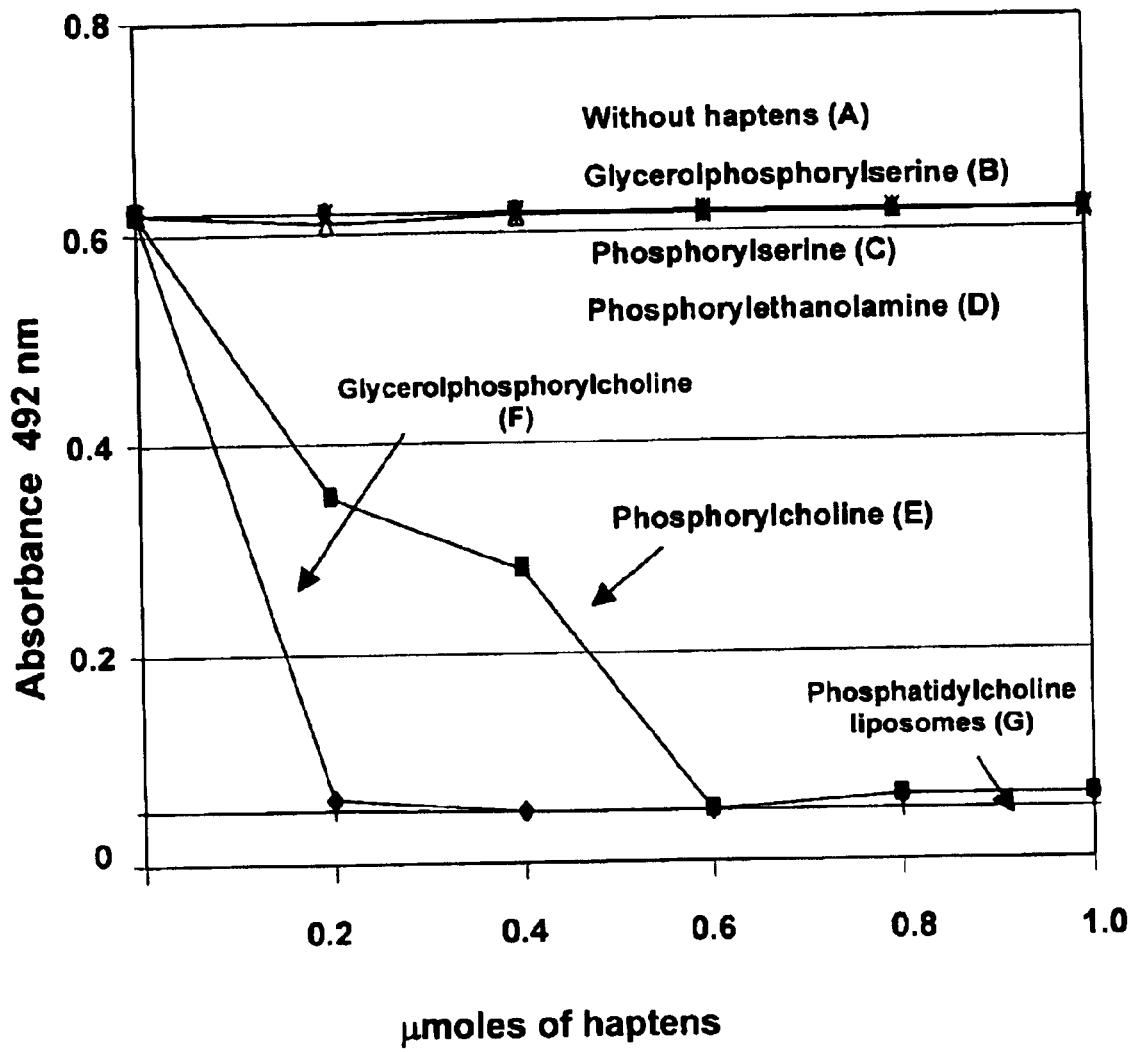
FIG. 14 illustrates the graphs of the inhibition of H308 monoclonal antibody with phosphorylcholine, glycerolphosphorylcholine, phosphorylserine, glycerolphosphorylserine or phosphorylethanolamine haptens. Furthermore, the reaction of H308 monoclonal antibody with liposomes made from phosphorylcholine is also showed.
Figure 15:
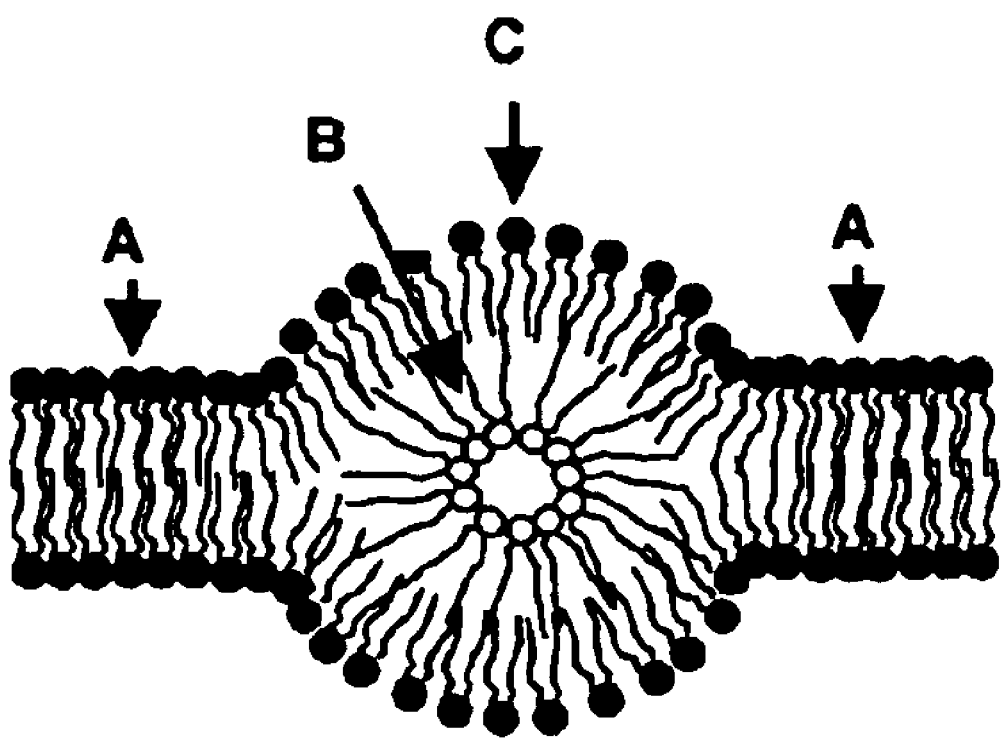
FIG. 15 is a scheme of the lipids associated in the molecular arrangement of bilayer and of inverted micella which is inserted in an open lipidic bilayer which constitute the lipidic particle on the whole. Arrows indicate the different molecular arrangements adopted by lipids.

Gycerolphosphorylcholine hapten at a concentration of 0.2 $\mu$moles produce an 100% inhibition in the immunoreaction of patients sera with lipidic particles in liposomes, in a similar way as it was described by the inhibition of H308 monoclonal antibody in FIG. 14 graphs, Example 6.

These results confirm that sera from patients with the antiphospholipid syndrome have anti-lipidic particles antibodies with an antigenic specificity similar to that of H308 monoclonal antibody, since they were inhibited in the same proportion by the gycerolphosphorylcholine hapten.

Studies in BALB/c female mice in which were simultaneously administered the H308 monoclonal antibody, which developed in these mice a pathology similar to human antiphospholipid syndrome as it was described in Example 4C, and the glycerol-phosphorylcholine hapten, showed a blockage in the development of the pathology in BALB/c female mice. H308 monoclonal antibody was administered by intraperitoneal injection of 1 $\mu$g each week during two months to BALB/c female mice, and simultaneously the glycerolphosphorylcholine hapten was administered at 2.5 mg/Kg, of body weight, doses by intravenous injection each 24 hs, for 2-months. With this treatment it was inhibited in 40% the development of mice pathology by H308 monoclonal antibody.

In accordance with the above-mentioned studies the therapeutically effective quantity of the inhibitor drug glycerol-phosphorylcholine is of 2.5 mg/Kg of body weight.

Example 7

Study by the Liposomal Cytofluorometry Method of the Stabilization of Liposomal Membranes that Prevent the Formation of Lipidic Particles and the Subsequent Binding of Anti-lipidic Particles Antibodies These studies were carried out with a modification in the liposomal cytofluorometry method with liposomes made from egg-yolk phosphatidylcholine:phosphatidate (2:1 molar ratio) in Tris-NaCl buffer (10 mM, 1 mM) pH 7, containing 0.1 $\mu$mol of phosphatidate, and treated with 0.2 mM chlorpromazine to induce lipidic particles formation, as antigens.

Immediately after the addition of the lipidic particles inducer drug chlorpromazine liposomes were incubated with different concentrations of the lipid bilayer stabilizers drugs spermidine or chloroquine. Liposomal preparations were incubated for 30 min at room temperature and were used as antigens. The reaction of these stabilized liposomes with H308 monoclonal antibody was analyzed by the liposomal cytofluorometry method as was described in Example 2A, in a FACSCalibur Flow Cytometer equipped with a single 488 nm argon laser beam (Beckton Dickinson).

Relative size and/or liposomal aggregation were analyzed in the FSC channel and the granularity or liposomal bilayers complexity in the SSC channel. Analysis of 10,000 liposomes was made in a logarithmic mode with the following detectors: FSC in E00, with a detector compensation threshold of 52 V and SSC of 401 V (Baeza et al., op. cit., 1995). The obtained data were analyzed with the Cellquest program (Beckton Dickinson).

Figure 16:
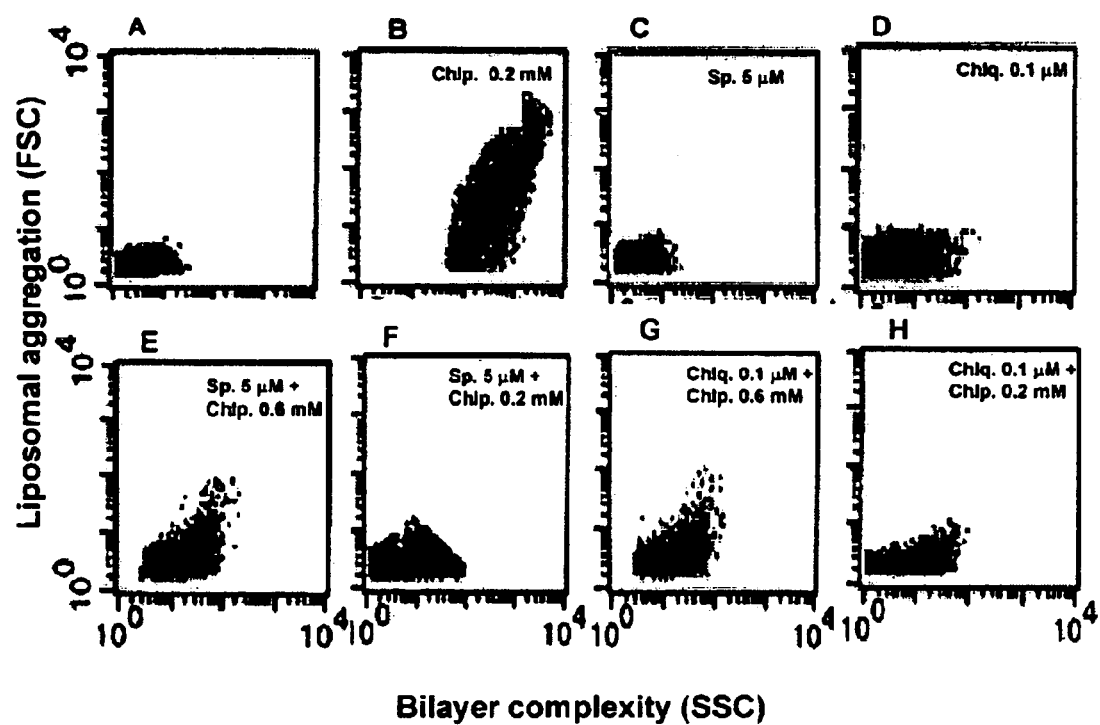
FIGS. 16A–16H illustrate the graphs of liposomal aggregation and liposomal bilayers complexity that analyze the lipidic bilayers stabilization of liposomal antigens made from PC:PA (2:1 mole ratio) treated with the lipidic particles inducer drugs chlorpromazine or procainamide and/or with the lipidic bilayer stabilizer drugs chloroquine or spermidine.

When egg-yolk phosphatidylcholine:phosphatidate (2:1 molar ratio) liposomes, in Tris-NaCl buffer (10 mM, 1 mM) pH 7, and containing 0.1 $\mu$mol of phosphatidate (A, FIG. 16), were treated with 0.2 mM chlorpromazine an 100-fold increase in SSC and FSC values were observed which showed the presence of lipidic particles and liposomal aggregation, respectively (B, FIG. 16).

In contrast, the incubation of egg-yolk phosphatidylcholine:phosphatidate (2:1 molar ratio) liposomes, in Tris-NaCl buffer (10 mM, 1 mM) pH 7, and containing 0.1 $\mu$mol of phosphatidate, with the stabilizer drugs spermidine (C, FIG. 16) or chloroquine (D, FIG. 16) do not produce any change in liposomal aggregation and in liposomal bilayers complexity because the graphs obtained were similar to that corresponding to liposomes in buffer solution (A, FIG. 16). However, when liposomes were incubated simultaneously with the lipidic particles inducer drug chlorpromazine and the lipidic bilayer stabilizer drugs spermidine (E, F, FIG. 16) or chloroquine (G, H, FIGS. 16) there were not lipidic particles formation neither liposomal aggregation. It can be observed that SSC and FSC values (E–H, FIG. 16) were very similar to those of liposomes in buffer solution, which showed SSC values smaller than 100 units; contrary to the graph that indicates the presence of lipidic particles, with SSC values higher than 1000 units is (B, FIG. 16).

These studies showed that spermidine is effective in stabilizing lipidic bilayers at concentrations 5 $\mu$M, this spermidine quantity blockage the formation of lipidic particles induced by chlorpromazine at concentrations of 0.2 mM and 0.6 mM, respectively (E, F, FIG. 16). For chloroquine, effective concentrations were even smaller, since this stabilizer drug produced liposomal stabilization at a concentration of 0.1 $\mu$M when the lipidic particles inducer drug chlorpromazine were used at 0.2 mM and 0.6 mM, respectively (G, H, FIG. 16).

When liposomes incubated with both drugs: the lipidic particles inducer drug and the lipidic bilayer stabilizer drug were used as antigens there was not any immunoreaction with the H308 monoclonal antibody, because the cytofluorometry graphs obtained were as those corresponding to liposomes alone and in absence of antibodies in: g, FIG. 3D; and i, FIG. 3E, instead of as those that indicate the reaction of H308 monoclonal antibody with lipidic particles in: b, FIG. 3A; and d, FIG. 3B.

These results indicate that liposomal membranes were stabilized by their interaction with lipidic bilayer stabilizers drugs spermidine or chloroquine in consequence they do not contain lipidic particles and therefore they do not react with H308 monoclonal antibody.

Example 7A

Study by the Cytofluorometry Method of the Cellular Membranes Stabilization that Prevents the Formation of Lipidic Particles and the Later Binding of Anti-lipidic articles Antibodies Ag4 mouse myeloma cells suspended in Tris-NaCl buffer (10 mM, 135 mM) pH 7, containing glucose 11 mM, were incubated with the lipidic particles inducer drug chlorpromazine 0.2 mM. Immediately after the addition of chlorpromazine the Ag4 mouse myeloma cells were incubated with different concentrations of the lipid bilayer stabilizer drugs spermidine or chloroquine for 30 min at room temperature. The reaction of these stabilized Ag4 mouse myeloma cells with H308 monoclonal antibody was analyzed by the cytofluorometry method in a FACSCalibur Flow Cytometer equipped with a single 488 run argon laser beam (Beckton Dickinson).

Relative size and/or Ag4 mouse myeloma cells aggregation were analyzed in the FSC channel and the granularity or cellular membranes complexity in the SSC channel. Analysis of 10,000 Ag8 mouse myeloma cells was made with the following detectors: FSC in E00 in lineal mode with an amplifier gain of 2 V, with a detector compensation threshold of 52 V, and SSC of 250 V. The obtained data were analyzed with the Cellquest program (Beckton Dickinson).

Results obtained with Ag4 mouse myeloma cells incubated with the lipidic particles inducer drug chlorpromazine and the lipid bilayer stabilizer drugs spermidine or chloroquine were similar to those described in FIG. 16 graphs. These results showed that Ag4 cellular membranes were stabilized by their interaction with lipidic bilayer stabilizers drugs spermidine or chloroquine in consequence they do not develop lipidic particles with chlorpromazine.

When Ag4 mouse myeloma cells incubated with both drugs: the lipidic particles inducer drug and the lipidic bilayer stabilizer drug were used as antigens there were not any immunoreaction with the H308 monoclonal antibody, in a similar way as was demonstrated for liposomes stabilized with the drugs spermidine or chloroquine in Example 7.

These results indicate that cellular membranes of Ag4 mouse myeloma cells stabilized by their interaction with spermidine or chloroquine do not develop lipidic particles and therefore by they do not react with the H308 monoclonal antibody.

Example 7B

Detection of the Lipidic Particles Reversion by the Lipidic Bilayer Stabilizer Drugs Spermidine and Chloroquine Examples 7 and 7A were repeated using as antigens egg-yolk phosphatidylcholine:phosphatidate (2:1 molar ratio) liposomes, in Tris-NaCl buffer (10 mM, 1 mM) pH 7, and containing 0.1 $\mu$mol of phosphatidate, or Ag4 mouse myeloma cells. Liposomal or cellular antigens were incubated with the lipidic particles inducer drug chlorpromazine 0.2 mM for 30 min at room temperature before the treatment with the lipidic bilayers stabilizer drugs spermidine or chloroquine. Stabilizer drugs were used at the concentrations used in Example 7A.

Cytofluorometric analysis showed that the formation of lipidic particles and the liposomal or cellular aggregation caused by chlorpromazine, which produce graphics similar to: B, FIG. 16, were reverted by the lipid bilayer stabilizers spermidine or chloroquine. This reversion that destroy lipidic particles in liposomal and cellular antigens produce graphics as those shown in: E, F, G, and H, FIG. 16, which showed lipids in bilayer molecular arrangements.

After lipidic particles reversion liposomal or cellular antigens do not show any reaction with H308 monoclonal antibody, due to the absence of lipidic particles in their surfaces.

These experiments showed that spermidine and chloroquine drugs have the action of prevent the formation of lipidic particles and additionally they can also destroy lipidic particles already formed. These findings are very important for the application of these stabilizer drugs in the treatment of human illnesses in which lipidic particles and/or anti-lipidic particles antibodies participate.

Studies in BALB/c female mice in which were simultaneously administered the H308 monoclonal antibody, which develop in these mice a pathology similar to human antiphospholipid syndrome as it was described in Example 4C, and one of the lipid bilayer stabilizer drugs spermidine or chloroquine, showed a delay in the development of this pathology. H308 monoclonal antibody was administered by intraperitoneal injection of 1 $\mu$g each week for 2-months to BALB/c female mice, and simultaneously the stabilizer drug chloroquine was administered at 2.5 mg/Kg, of body weight, oral doses each 24 hs, during two months. With this treatment it was delayed the development of mice pathology induced by H308 monoclonal antibody. It is possible that modifying the doses of stabilizers drugs that are applied to mice it is possible to prevent the development of these illnesses. The chloroquine dose used was similar to the one used in humans in the treatment of rheumatoid arthritis and of systemic lupus erythematosus.

Spermidine was administered, as chlorhydrate, in a dose of 1 mg/Kg, of body weight, by intraperitoneal injection each 24 hs, during two months. Using this spermidine dose results similar to those described with chloroquine were obtained.

According to the above-mentioned studies the therapeutically effective quantity of the lipidic bilayer stabilizer drug chloroquine is of 2.5 mg/Kg, of body weight, and of spermidine is of 1 mg/Kg, of body weight.

In accordance with the information described in this work, one will be able to observe that the use of antibodies obtained by using lipidic structures different to lipid bilayers to determine cellular physiologic states and for the diagnosis and/or treatment of diseases has been designed to allow an early detection of diseases associated with antiphospholipid antibodies and, as a consequence, to allow a treatment to prevent, to stop and to revert this disease; and it will be evident for any expert in the matter that the modalities that here are presented, they are only illustrative and they will not be interpreted in a limitative form of the present invention, since there are possible other numerous changes in their details and particularities, without moving away from the scope of the invention.

Though it has been illustrated and described specific embodiments of the invention, it is necessary to emphasize that are possible other numerous modifications to the invention, as they can be the use of different mice strains, lipids to obtain the liposomes, immunization methods and methods for obtaining hybridomas, diverse reagents for the kit of diagnosis and/or diverse illnesses associated with antiphospholipid antibodies. Therefore, the present invention should not be considered as restricted except for which demands the previous technique and for the spirit of the annexed claims.

What is claimed is:

1. A diagnostic method for indirectly determining the presence of lipidic particles in cell membranes from a sample suspected of having anti-lipidic particle antibodies from an individual suspected of suffering primary antiphospholipid syndrome or a disease associated with secondary antiphospholipid syndrome, wherein the presence of said lipidic particles in cell membranes allows diagnosis of whether said individual is developing an illness associated with the presence of antiphospholipid antibodies though said individual does not present anti-cardiolipin antibodies, lupus anti-coagulant, anti-DNA antibodies or anti-nuclear antibodies, comprising:

a) removing a sample suspected of having anti-lipidic particle antibodies from said individual testing said sample from said individual to determine that said sample does not present anti-cardiolipin antibodies, lupus anti-coagulant, anti-DNA antibodies or anti-nuclear antibodies;

b) combining the removed sample with an antigen having said lipidic particles, said lipidic particles being immersed in a bilayer structure but not forming part of the bilayer structure, wherein said combining is under conditions effective to permit binding of anti-lipidic particle antibodies present in the sample to said antigen thereby forming a first mixture;

c) adding to the first mixture a detectable-labeled reagent useful for detecting binding of anti-lipidic particle antibodies to the antigen having lipidic particles thereby forming a second mixture;

d) detecting the presence of anti-lipidic particle antibodies in the sample bound to the antigen having lipidic particles in the second mixture, wherein said detection of anti-lipidic particle antibodies bound to the antigens having lipidic particles is an indirect indication of the presence of lipidic particles in cell membranes of said individual; and e) correlating the presence of anti-lipidic particle antibodies in the second mixture with immune damage in cell membranes having lipidic particles of said individual as one of the first events in illness associated with the presence of antiphospholipid antibodies.

2. The method of claim 1, wherein the detectable-labeled reagent comprises detectable-labeled polyvalent anti-human immunoglobulins second antibodies which bind to the anti-lipidic particle antibodies.

3. The method of claim 2, wherein the detectable-labeled anti-human immunoglobulin second antibodies comprises at least one anti-human immunoglobulin antibody directed against at least one human immunoglobulin class, and the presence of anti-lipidic particle antibodies is determined with one antibody selected from the group consisting of anti-lipidic particles IgG, IgM and IgA antibodies.

4. The method of claim 1, wherein the detectable-labeled reagent comprises one component selected from the group consisting of enzymes and fluorochromes, said component being attached to one element selected from the group consisting of polyvalent anti-immunoglobulin, anti-IgG, IgM and IgA immunoglobulin second antibodies.

5. The method of claim 1, wherein the detection of the presence of anti-lipidic particle antibodies in the sample from said individual is carried out using a protocol selected from the group consisting of ELISA, cytofluorometry and immunofluorescence.

6. The method of claim 1, wherein removing a sample suspected of having anti-lipidic particle antibodies from said individual comprises removing an antibody porter.

7. The method of claim 6, wherein the antibody porter comprises plasma or serum.

8. The method of claim 1, wherein said lipidic particles have a structural arrangement which is immersed in a bilayer structure of liposomes or cells without forming a part of said bilayer structure.

9. The method of claim 8 wherein the structural arrangement of said lipidic particles is selected from the group consisting of arrangements in hexagonal II and micellar phases.

* * * * *